United States Patent
Mitter et al.

(10) Patent No.: US 9,364,005 B2
(45) Date of Patent: Jun. 14, 2016

(54) PLANT-ENDOPHYTE COMBINATIONS AND USES THEREFOR

(71) Applicant: Austrian Institute of Technology GmbH, Vienna (AT)

(72) Inventors: Birgit Mitter, Gießhübl bei Wien (AT); Milica Pastar, Vienna (AT); Angela Sessitsch, Vienna (AT)

(73) Assignee: AIT AUSTRIAN INSTITUTE OF TECHNOLOGY GMBH, Tulln (AT)

( * ) Notice: Subject to any disclaimer, the term of this patent is extended or adjusted under 35 U.S.C. 154(b) by 0 days.

(21) Appl. No.: 14/315,804

(22) Filed: Jun. 26, 2014

(65) Prior Publication Data

US 2015/0373992 A1    Dec. 31, 2015

(51) Int. Cl.
*A01N 63/02* (2006.01)
*A01N 63/00* (2006.01)

(52) U.S. Cl.
CPC ............... *A01N 63/02* (2013.01); *A01N 63/00* (2013.01)

(58) Field of Classification Search
CPC .............................. A01N 63/02; A01N 63/01
USPC ........................................................ 800/298
See application file for complete search history.

(56) References Cited

U.S. PATENT DOCUMENTS

| | | | |
|---|---|---|---|
| 5,919,447 | A | 7/1999 | Marrone et al. |
| 6,337,431 | B1 | 1/2002 | Tricoli et al. |
| 6,495,133 | B1 * | 12/2002 | Xue .............................. 424/93.5 |
| 6,681,186 | B1 | 1/2004 | Denisov et al. |
| 6,689,880 | B2 | 2/2004 | Chen et al. |
| 7,335,816 | B2 | 2/2008 | Kraus et al. |
| 7,341,868 | B2 * | 3/2008 | Chopade et al. ........... 435/320.1 |
| 7,485,451 | B2 | 2/2009 | VanderGheynst et al. |
| 7,555,990 | B2 | 7/2009 | Beaujot |
| 7,632,985 | B2 | 12/2009 | Malven et al. |
| 7,977,550 | B2 | 7/2011 | West et al. |
| 8,455,198 | B2 | 6/2013 | Gao et al. |
| 8,455,395 | B2 | 6/2013 | Miller et al. |
| 8,465,963 | B2 | 6/2013 | Rolston et al. |
| 8,728,459 | B2 | 5/2014 | Isawa et al. |
| 2005/0072047 | A1 | 4/2005 | Conkling et al. |
| 2007/0028318 | A1 | 2/2007 | Livore et al. |
| 2007/0055456 | A1 | 3/2007 | Raftery et al. |
| 2008/0289060 | A1 | 11/2008 | De Beuckeleer et al. |
| 2012/0108431 | A1 | 5/2012 | Williams et al. |
| 2014/0109249 | A1 | 4/2014 | Turner et al. |
| 2014/0115731 | A1 | 4/2014 | Turner et al. |

FOREIGN PATENT DOCUMENTS

| | | |
|---|---|---|
| CA | 1041788 | 11/1978 |
| CA | 1229497 | 11/1987 |
| EP | 0192342 | 8/1986 |
| EP | 0818135 | 1/1998 |
| EP | 2676536 | 12/2013 |
| WO | WO 01/83818 | 11/2001 |
| WO | WO 2008/103422 | 8/2008 |
| WO | WO 2013/090628 | 6/2013 |
| WO | WO 2013/122473 | 8/2013 |
| WO | WO 2013/190082 | 12/2013 |
| WO | WO 2014/046553 | 3/2014 |

OTHER PUBLICATIONS

Trotel-Aziz et al. 2008 Encironmental and Experimental Botany 6:21-32.*
Xue et al. 2009 Biological Control 48:252-258.*
Abarenkov et al., "PlutoF—a Web Based Workbench for Ecological and Taxonomic Research, with an Online Implementation for Fungal ITS Sequences," Evol Bioinform Online, 2010, 6: 189-196.
Abarenkov et al., "The Unite database for molecular identification of fungi—recent updates and future perspectives," New Phytol., 2010, 186(2):281-285.
Ahmad et al., "Screening of free-living rhizospheric bacteria for their multiple plant growth promoting activities," Microbiol Res., 2008, 163(2):173-181.
Amann et al., "The identification of microorganisms by fluorescence in situ hybridisation," Curr Opin Biotechnol., 2001, 12(3):231-236.
Apel and Hirt, "Reactive oxygen species: metabolism, oxidative stress, and signal transduction," Annu Rev Plant Biol., 2004, 55:373-99.
Bacon and Hinton, "Isolation, In Planta Detection, and Uses of Endophytic Bacteria for Plant Protection", Chapter in Manual of Environmental Microbiology, 3rd Edition (2007): 638-647.
Baker and Smith, "Dynamics of Seed Transmission of Plant Pathogens," Annu Rev Phytopathol., 1966, 4:311-334.
Block et al., "Seed Transmission of Pantoea stewartii in Field and Sweet Corn," Plant Disease, 1998, 82(7):775-780.
Bulgarelli et al., "Structure and Functions of the Bacterial Microbiota of Plants," Annu Rev Plant Biol., 2013, 64:807-38.
Caporaso et al., "Ultra-high-throughput microbial community analysis on the Illumina HiSeq and MiSeq platforms," ISME J., 2102, 6(8):1621-1624.
Cavalier-Smith, "A revised six-kingdom system of life," Biol Rev Camb Philos Soc., 1998, 73(3):203-66.
Cha et al., "Production of acyl-homoserine lactone quorum-sensing signals by gram-negative plant-associated bacteria," Mol Plant Microbe Interact., 1998, 11:1119-1129.
Chernin et al., "Chitinolytic activity in Chromobacterium violaceum: substrate analysis and regulation by quorum sensing," J Bacteriol., 1998, 180(17):4435-4441.

(Continued)

*Primary Examiner* — Li Zheng
(74) *Attorney, Agent, or Firm* — Fenwick & West LLP

(57) ABSTRACT

The disclosure provides materials and methods for conferring improved plant traits or benefits on plants. The materials can include a formulation comprising an exogenous endophytic bacterial population, which can be disposed on an exterior surface of a seed or seedling, typically in an amount effective to colonize the plant. The formulations can include at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient.

16 Claims, 7 Drawing Sheets

(56) References Cited

OTHER PUBLICATIONS

Clark et al., "Improved histochemical techniques for the detection of Acremonium coenophilum in tall fescue and methods of in vitro culture of the fungus," J. Microbiol Methods, 1983, 1:149-155.
Clough and Bent, "Floral dip: a simplified method for Agrobacterium-mediated transformation of Arabidopsis thaliana," Plant J., 1998, 16(6): 735-743.
Cox, "Deferration of laboratory media and assays for ferric and ferrous ions," Methods Enzymol., 1994, 235:315-329.
Craine et al., "Global diversity of drought tolerance and grassland climate-change resilience," Nature Climate Change, 2013, 3:63-67.
Danhorn and Fuqua, "Biofilm formation by plant-associated bacteria," Annu Rev Microbiol., 2007, 61:401-422.
Daniels et al., "Quorum signal molecules as biosurfactants affecting swarming in Rhizobium etli," PNAS, 2006, 103(40):14965-14970.
de Freitas et al., "Phosphate-solubilizing rhizobacteria enhance the growth and yield but not phosphorus uptake of canola (Brassica napus L.)," Biol Fertil Soils, 1997, 24(4):358-364.
Dennis and Webster, "Antagonistic properties of species groups of Trichoderma I. Production of non-volatile antibiotics," Trans Brit Mycol Soc, 1971, 57:25-39.
Djordjevic et al., "Microtiter plate assay for assessment of Listeria monocytogenes biofilm formation," Appl Environ Microbiol., 2002, 68(6):2950-2958.
Don and Pemberton, "Properties of six pesticide degradation plasmids isolated from Alcaligenes paradoxus and Alcaligenes eutrophus," J Bacteriol., 1981, 145(2):681-686.
Eberhard et al., "Structural identification of autoinducer of Photobacterium fischeri luciferase," Biochem., 1981, 20(9):2444-2449.
Edgar, "Search and clustering orders of magnitude faster than BLAST," Bioinformatics, 2010, 26(19):2460-2461.
Edgar, "UPARSE: highly accurate OTU sequences from microbial amplicon reads," Nat Methods, 2013, 10(10):996-8.
Endre et al., "A receptor kinase gene regulating symbiotic nodule development," Nature, 2002, 417(6892):962-966.
Faria et al., "Endophytic bacteria isolated from orchid and their potential to promote plant growth," World J Microbiol Biotechnol., 2013, 29(2):217-221.
Fiehn et al., "Metabolite profiling for plant functional genomics," Nature Biotechnol., 2000, 18(11):1157-1161.
Fierer et al., "Cross-biome metagenomic analyses of soil microbial communities and their functional attributes," Proc Natl Acad Sci USA, 2012, 109(52):21390-21395.
Fincher, "Molecular and Cellular Biology Associated with Endosperm Mobilization in Germinating Cereal Grains," Annu Rev Plant Physiol Plant Mol Biol., 1989, 40:305-46.
Fisher et al., "Isolation and characterization of the pesticide-degrading plasmid pJP1 from Alcaligenes paradoxus," J Bacteriol., 1978, 135(3):798-804.
Fulthorpe et al., "Distantly sampled soils carry few species in common," ISME J., 2008, 2(9):901-910.
Gantner et al., "Novel primers for 16S rRNA-based archaeal community analyses in environmental samples," J Microbiol Methods, 2011, 84(1):12-18.
Gao et al., "Quantitation of major human cutaneous bacterial and fungal populations," J Clin Microbiol., 2010, 48(10):3575-3581.
Gasser et al., "Ecology and characterization of polyhydroxyalkanoate-producing microorganisms on and in plants," FEMS Microbiol Ecol., 2010, 70:142-150.
Gilmour et al., "Overexpression of the Arabidopsis CBF3 transcriptional activator mimics multiple biochemical changes associated with cold acclimation," Plant Physiol., 2000, 124(4):1854-1865.
Gitaitis and Walcott, "The epidemiology and management of seedborne bacterial diseases," Annu Rev Phytopathol., 2007, 45:371-97.
Haake et al., "Transcription factor CBF4 is a regulator of drought adaptation in Arabidopsis," Plant Physiol., 2002, 130(2):639-648.
Haas and Holloway, "R factor variants with enhanced sex factor activity in Pseudomonas aeruginosa," Mol Gen Genet., 1976, 144(3):243-251.
Hallman et al., "Bacterial endophytes in agricultural crops," Canadian J Microbiol., 1997, 43(10):895-914.
Hardegree and Emmerich, "Effect of polyethylene glycol exclusion on the water potential of solution-saturated filter paper," Plant Physiol., 1990, 92:462-466.
Hardoim et al., "Assessment of rice root endophytes and their potential for plant growth promotion," In: Hardoim PR, editor. Bacterial endophytes of rice—their diversity, characteristics and perspectives. Groningen, 2011, pp. 77-100.
Hardoim et al., "Dynamics of Seed-Borne Rice Endophytes on Early Plant Growth Stages," PLoS One, 2012, 7(2):e30438, 13 pages.
Hepler et al., "Polarized cell growth in higher plants," Annu Rev Cell Dev Biol., 2001, 17:159-87.
Hiatt, III et al., "Tall fescue endophyte detection: Tissue immunoblot test kit compared with microscopic analysis," Crop Science, 1999, 39:796-799.
Hibbett et al., "A higher level phylogenetic classification of the Fungi," Mycol Res., 2007, 111(5):509-547.
Hill and Roach, "Endophyte Survival during Seed Storage: Endophyte—Host Interactions and Heritability," Crop Sci., 2009, 49:1425-1430.
Hill and Roach, "Endophyte Survival during Seed Storage: Endophyte—Host Interactions and Heritability," PowerPoint, Dept. Crop Soil Sciences, University of Georgia, Nov. 2012, 3 pages.
Idris et al., "Efficacy of rhizobacteria for growth promotion in sorghum under greenhouse conditions and selected modes of action studies," J Agr Sci., 2009, 147:17-30.
Imoto et al., "Comprehensive approach to genes involved in cell wall modifications in Arabidopsis thaliana," Plant Mol Biol., 2005, 58(2):177-192.
Johnston-Monje and Raizada, "Conservation and diversity of seed associated endophytes in Zea across boundaries of evolution, ethnography and ecology," PLoS One, 2011, 6(6):e20396, 22 pages.
Johnston-Monje and Raizada, "Plant and Endophyte Relationships: Nutrient Management," Comprehensive Biotechnol., 2011, 4:713-727.
Johnston-Monje, "Microbial Ecology of Endophytic Bacteria in Zea Species as Influenced by Plant Genotype, Seed Origin, and Soil Environment," Thesis, University of Guelph, 2011, 230 pages.
Jones, "Fresh Isolates of Actinomycetes in which the Presence of Sporogenous Aerial Mycelia is a Fluctuating Characteristic," J Bacteriol., 1949, 57(2):141-5.
Kang et al., "Members of the Arabidopsis dynamin-like gene family, ADL1, are essential for plant cytokinesis and polarized cell growth," Plant Cell, 2003, 15(4):899-913.
Kasana et al., "A rapid and easy method for the detection of microbial cellulases on agar plates using gram's iodine," Curr Microbiol., 2008, 57(5):503-507.
Kruger et al., "DNA-based species level detection of Glomeromycota: one PCR primer set for all arbuscular mycorrhizal fungi," New Phytol., 2009, 183(1):212-23.
Lanver et al., "Sho1 and Msb2-related proteins regulate appressorium development in the smut fungus Ustilago maydis," Plant Cell, 2010, 22(6):2085-2101.
Laus et al., "Role of cellulose fibrils and exopolysaccharides of Rhizobium leguminosarum in attachment to and infection of Vicia sativa root hairs," Mol Plant Microbe Interact., 2005, 18(6):533-538.
Leonard et al., "Random Mutagenesis of the Aspergillus oryzae Genome Results in Fungal Antibacterial Activity," Int J Microbiol., 2013, 2013:901697, 6 pages.
Li et al., "Expression of a novel chitinase by the fungal endophyte in Poa ampla," Mycologia, 2004, 96(3):526-536.
Liu et al., "A novel screening method for isolating exopolysaccharide-deficient mutants," Appl Environ Microbiol., 1998, 64(11):4600-4602.
Liu et al., "Investigation on diversity and population succession dynamics of endophytic bacteria from seeds of maize (Zea mays L., Nongda108) at different growth stages," Ann Microbiol., 2013, 63:71-79.

(56) References Cited

OTHER PUBLICATIONS

Liu et al., "Osmotin overexpression in potato delays development of disease symptoms," Proc Natl Acad Sci USA, 1994, 91(5):1888-1892.
Long et al., "The structure of the culturable root bacterial endophyte community of Nicotiana attenuata is organized by soil composition and host plant ethylene production and perception," New Phytol., 2010, 185(2):554-567.
Lopez-Lopez et al., "Phaseolus vulgaris seed-borne endophytic community with novel bacterial species such as *Rhizobium endophyticum* sp. nov.," Systematic Appl Microbiol., 2010, 33:322-327.
Lorck, "Production of Hydrocyanic Acid by Bacteria," Physiol Plant, 1948, 1:142-146.
Lugtenberg and Kamilova, "Plant-Growth-Promoting Rhizobacteria," Ann. Rev. Microbiol., 2009, 63:541-556.
Lundberg et al., "Defining the core Arabidopsis thaliana root microbiome," Nature, 2012, 488(7409):86-90.
Lundberg et al., "Practical innovations for high-throughput amplicon sequencing," Nat Methods, 2013, 10:999-1002.
Madi and Henis, "Aggregation in Azospirillum brasilense Cd: Conditions and factors involved in cell-to-cell adhesion," Plant Soil, 1989, 115(1):89-98.
Männistö and Häggblom, "Characterization of psychrotolerant heterotrophic bacteria from Finnish Lapland," Syst Appl Microbiol., 2006, 29(3):229-243.
Manter and Vivanco, "Use of the ITS primers, ITS1F and ITS4, to characterize fungal abundance and diversity in mixed-template samples by qPCR and length heterogeneity analysis," J Microbiol Methods, Oct. 2007, 71(1):7-14.
Marasco et al., "A drought resistance-promoting microbiome is selected by root system under desert farming," PLoS One, 2012, 7(10):e48479, 14 pages.
Márquez et al., "A virus in a fungus in a plant: three-way symbiosis required for thermal tolerance," Science, 2007, 315(5811):513-515.
Mastretta et al., "Endophytic Bacteria from seeds of Nicotiana Tabacum can reduce Cadmium Phytotoxicity," Intl J Phytoremediation, 2009, 11:251-267.
Mateos et al., "Cell-associated pectinolytic and cellulolytic enzymes in Rhizobium leguminosarum biovar trifolii," Appl Environ Microbiol., 1992, 58(6):1816-1822.
McDonald et al., "An improved Greengenes taxonomy with explicit ranks for ecological and evolutionary analyses of bacteria and archaea," ISME J., 2012, 6(3):610-8.
McGuire et al., "Digging the New York City Skyline: soil fungal communities in green roofs and city parks," PloS One, 2013, 8:e58020, 13 pages.
Medina and Baresi, "Rapid identification of gelatin and casein hydrolysis using TCA," J Microbiol Methods, 2007, 69(2):391-393.
Mehnaz et al., "Growth promoting effects of corn (*Zea mays*) bacterial isolates under greenhouse and field conditions," Soil Biol Biochem., 2010, 42:1848-1856.
Michel and Kaufmann, "The osmotic potential of polyethylene glycol 6000," Plant Physiol., 1973, 51(5):914-916.
Mohiddin and Khan, "Tolerance of fungal and bacterial biocontrol agents to six pesticides commonly used in the control of soil borne plant pathogens," African Journal of Agricultural Research, 2013, 8(43):5331-5334.
Mousa and Raizada, "The diversity of anti-microbial secondary metabolites produced by fungal endophytes: an interdisciplinary perspective," Front Microbiol., Mar. 2013, 4:65, 18 pages.
Mundt and Hinkle, "Bacteria within ovules and seeds," Appl Environ Microbiol., 1976, 32(5):694-8.
Nelson, "Microbial dynamics and interactions in the spermosphere," Ann. Rev. Phytopathol., 2004, 42:271-309.
Nikolcheva and Bärlocher, "Taxon-specific fungal primers reveal unexpectedly high diversity during leaf decomposition in a stream," Mycological Progress, 2004, 3(1):41-49.
Normander and Prosser, "Bacterial Origin and Community Composition in the Barley Phytosphere as a Function of Habitat and Presowing Conditions," Appl Environ Microbiol., Oct. 2000, 66(10):4372-4377.
Okunishi et al., "Bacterial flora of endophytes in the maturing seeds of cultivated rice (*Oryza sativa*)," Microbes and Environment, 2005, 20:168-177.
Partida-Martinez and Heil, "The microbe-free plant: fact or artifact?" Front Plant Sci., Dec. 2011, 2:100, 16 pages.
Pearson, "Rapid and sensitive sequence comparison with FASTP and FASTA," Methods Enzymol., 1990, 183:63-98.
Perez-Fernandez et al., "Simulation of germination of pioneer species along an experimental drought gradient," J Environ Biol., 2006, 27(4):669-685.
Perez-Miranda et al., "O-CAS, a fast and universal method for siderophore detection," J Microbiol Methods, 2007, 70(1):127-131.
Phalip et al., "A method for screening diacetyl and acetoin-producing bacteria on agar plates," J Basic Microbiol., 1994, 34(4):277-280.
Philippot et al., "Going back to the roots: the microbial ecology of the rhizosphere," Nat Rev Microbiol., Nov. 2013, 11:789-799.
Pillay and Nowak, "Inoculum density, temperature, and genotype effects on in vitro growth promotion and epiphytic and endophytic colonization of tomato (*Lycopersicon esculentum* L.) seedlings inoculated with a pseudomonad bacterium," Can J Microbiol., 1997, 43:354-361.
Quadt-Hallmann et al., "Bacterial endophytes in cotton: mechanisms of entering the plant," Can J Microbiol., 1997, 43:577-582.
R Core Team, "R: A Language and Environment for Statistical Computing," R Foundation for Statistical Computing, Vienna, Austria, May 2013, ISBN: 3-900051-07-0. Available online at http://www.R-25 project.org/, 3604 pages.
Reiter et al., "Response of endophytic bacterial communities in potato plants to infection with *Erwinia carotovora* subsp. Atroseptica," Appl Environ Microbiol., 2001, 68:2261-2268.
Rodriguez et al., "Expression of a mineral phosphate solubilizing gene from Erwinia herbicola in two rhizobacterial strains," J Biotechnol., 2001, 84:155-161.
Rodriguez et al., "Stress tolerance in plants via habitat-adapted symbiosis," ISME J., 2008 2(4):404-416.
Roessner et al., "Metabolic profiling allows comprehensive phenotyping of genetically or environmentally modified plant systems," Plant Cell, 2001, 13(1):11-29.
Rosado et al., "Phenotypic and genetic diversity of Paenibacillus azotofixans strains isolated from the rhizoplane or rhizosphere soil of different grasses," J App Microbiol., 1998, 84:216-226.
Rosenblueth et al., "Seed Bacterial Endophytes: Common Genera, Seed-to-Seed Variability and Their Possible Role in Plants," Proc. XXVIIIth IHC—IS on Envtl., Edaphic & Gen. Factors; Affecting Plants, Seeds and Turfgrass, Acta Hort. 938, ISHS 2012, pp. 39-48.
Ross et al., "Multiplexed protein quantitation in *Saccharomyces cerevisiae* using amine-reactive isobaric tagging reagents," Mol Cell Proteomics, 2004, 3(12):1154-1169.
Saleem et al., "Perspective of plant growth promoting rhizobacteria (PGPR) containing ACC deaminase in stress agriculture," J Ind Microbiol Biotechnol., Oct. 2007, 34(10):635-648.
Samac and Graham, "Recent advances in legume-microbe interactions: recognition, defense response, and symbiosis from a genomic perspective," Plant Physiol., 2007, 144(2):582-587.
Sarwar et al., "Tryptophan dependent biosynthesis of auxins in soil," Plant Soil, 1992, 147:207-215.
Schmieder and Edwards, "Quality control and preprocessing of metagenomic datasets," Bioinformatics, 2011, 27(6):863-864.
Schoch et al., "Nuclear ribosomal internal transcribed spacer (ITS) region as a universal DNA barcode marker for Fungi," Proc Natl Acad Sci USA, 2012, 109(16):6241-6246.
Schwyn and Neilands, "Universal Chemical Assay for the Detection and Determination of Siderophores," Curr Microbiol., 1987, 43:57-58.
Shapiro-Ilan et al., "The potential for enhanced fungicide resistance in Beauveria bassiana through strain discovery and artificial selection," J Invertebr Pathol., 2002, 81(2):86-93.

(56) References Cited

OTHER PUBLICATIONS

Soares et al., "Screening of Bacterial Strains for Pectinolytic Activity: Characterization of the Polygalacturonase Produced by *Bacillus* SP," Revista de Microbiolgia, 1999, 30(4):299-303.

Souleimanov et al., "The major Nod factor of Bradyrhizobium japonicum promotes early growth of soybean and corn," J. Exp. Bot., 2002, 53:1929-1934.

Spiekermann et al., "A sensitive, viable-colony staining method using Nile red for direct screening of bacteria that accumulate polyhydroxyalkanoic acids and other lipid storage compounds," Arch Microbiol., 1999, 171(2):73-80.

Staudt et al., "Variations in exopolysaccharide production by Rhizobium tropici," Arch Microbiol., 2012, 194(3):197-206.

Sturz et al., "Weeds as a source of plant growth promoting rhizobacteria in agricultural soils," Can J Microbiol., 2001, 47:1013-1024.

Suto et al., "Endophytes as producers of xylanase," J Biosci Bioeng., 2002, 93:88-90.

Teather and Wood, "Use of Congo red-polysaccharide interactions in enumeration and characterization of cellulolytic bacteria from the bovine rumen," Appl Environ Microbiol., 1982, 43:777-780.

Thomas et al., "Development of resistance to chlorhexidine diacetate in Pseudomonas aeruginosa and the effect of a "residual" concentration," J Hosp Infect., 2000, 46(4):297-303.

Thomashow, "So what's new in the field of plant cold acclimation? Lots!," Plant Physiol., 2001, 125: 89-93.

Truyens et al., "Changes in the population of seed bacteria of transgenerationally Cd-exposed *Arabidopsis thaliana*," Plant Biol., 2013, 15:971-981.

Usadel and Fernie, "The plant transcriptome-from integrating observations to models," Front Plant Sci., 2013, 4:48, 3 pages.

Vacheron et al., "Plant growth-promoting rhizobacteria and root system functioning," Frontiers Plant Sci., Sep. 2013, 4:356, 19 pages.

van der Lelie et al., "Poplar and its Bacterial Endophytes: Coexistence and Harmony," Critical Rev Plant Sci., 2009, 28:346-358.

Vining et al., "Methylome reorganization during in vitro dedifferentiation and regeneration of Populus trichocarpa," BMC Plant Biol., 2013, 13:92, 15 pages.

Wang et al., "Monitoring in planta bacterial infection at both cellular and whole-plant levels using the green fluorescent protein variant GFPuv," New Phytol., 2007, 174(1): 212-23.

Wang et al., "Naive Bayesian classifier for rapid assignment of rRNA sequences into the new bacterial taxonomy," Appl Environ Microbiol., 2007, 73(16):5261-7.

Weaver et al., "Characterization of Rhodopseudomonas capsulata," Arch Microbiol., 1975, 105(3):207-216.

Welty et al., "Influence of Moisture Content, Temperature, and Length of Storage on Seed Germination and Survival of Endophytic Fungi in Seeds of Tall Fescue and Perennial Ryegrass," Phytopathyol., 1987, 77:893-900.

White JR et al., "A proposed mechanism for nitrogen acquisition by grass seedlings through oxidation of symbiotic bacteria," Symbiosis, Jul. 2012, 57(3):161-171.

Wiegand, et al., "Agar and broth dilution methods to determine the minimal inhibitory conventration (MIC) of antimicrobial substances," Nature Protocols, 2008, 3(.2):163-175.

Xu et al., "Bacterial community compositions of tomato (*Lycopersicum esculentum* Mill.) seeds and plant growth promoting activity of ACC deaminase producing Bacillus subtilis (HYT-12-1) on tomato seedlings," World J Microbiol Biotechnol., 2014, 30:835-845.

Zimmerman and Vitousek, "Fungal endophyte communities reflect environmental structuring across a Hawaiian landscape," Proc Natl Acad Sci USA, 2012, 109(32):13022-13027.

Zúñriiga et al., "Quorum sensing and indole-3-acetic acid degradation play a role in colonization and plant growth promotion of *Arabidopsis thaliana* by Burkholderia phytofirmans PsJN," Mol Plant Microbe Interact., 2013, 26:546-553.

\* cited by examiner

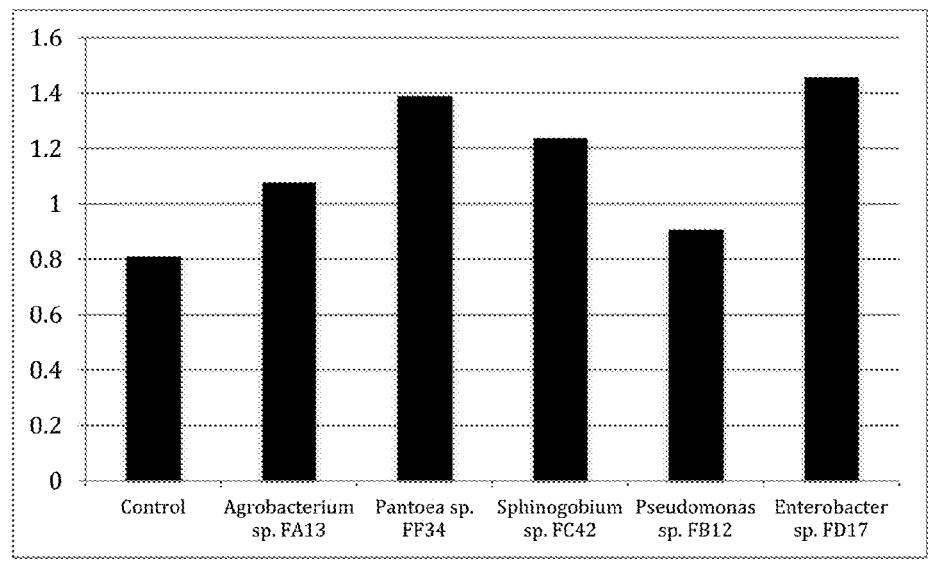
FIG. 1A Root Biomass
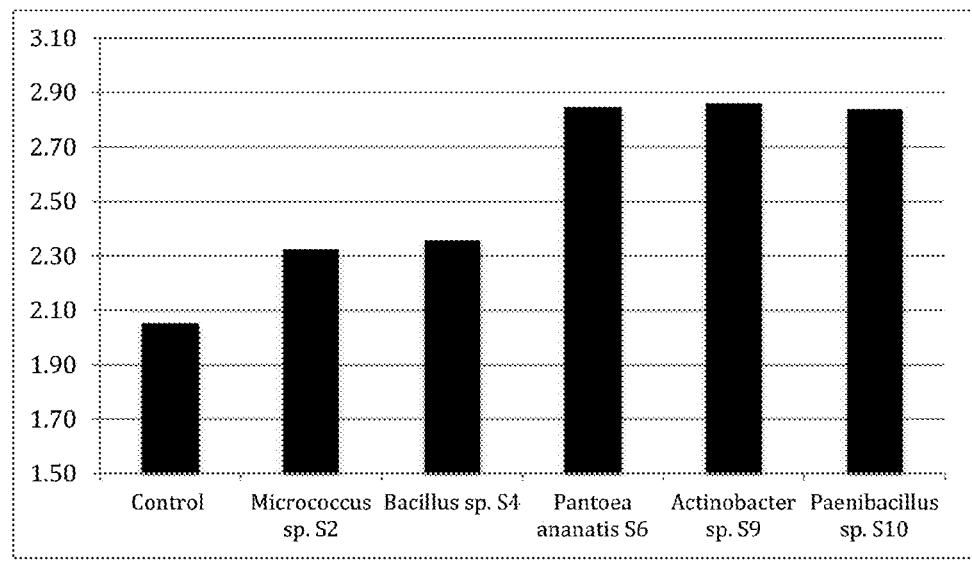

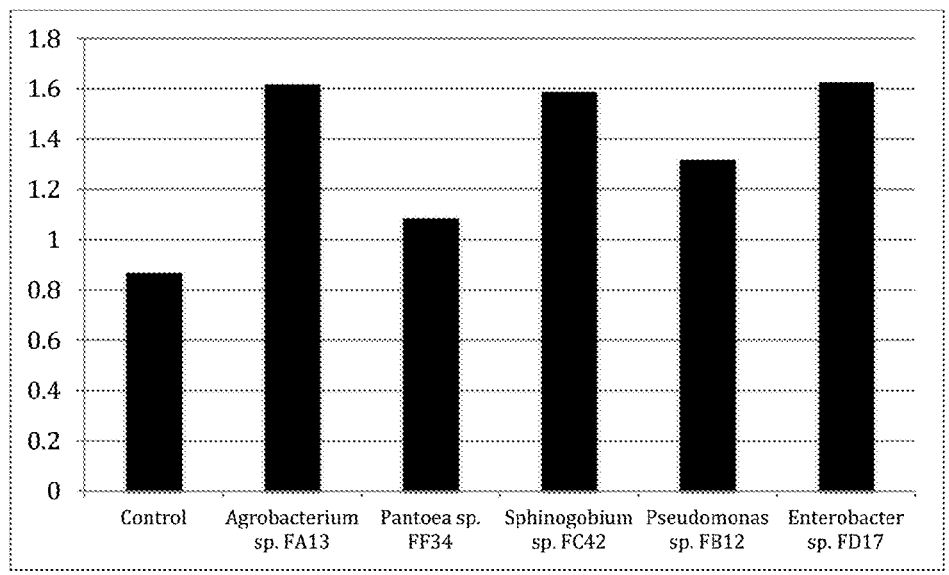
FIG. 1B Shoot biomass
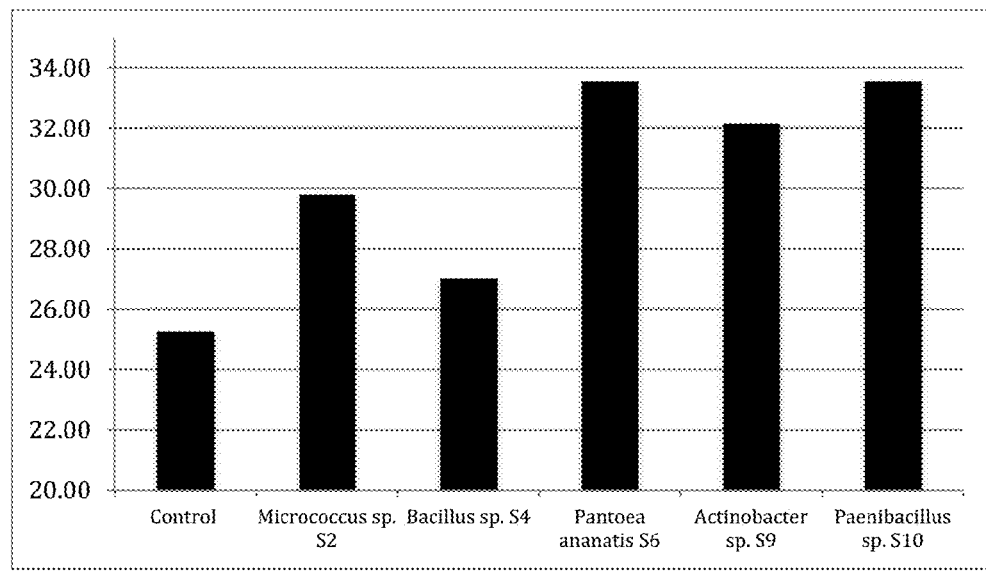
FIG. 1C Total Biomass

SEQUENCE LISTING

<160> NUMBER OF SEQ ID NOS: 10

<210> SEQ ID NO 1
<211> LENGTH: 1355
<212> TYPE: DNA
<213> ORGANISM: Agrobacterium sp.

<400> SEQUENCE: 1

```
atagcagtcg acgccccgca ggggagtggc agacgggtga gtaacgcgtg ggaacatacc      60
ctttcctgcg gaatagctcc gggaaactgg aattaatacc gcatacgccc tacgggggaa     120
agatttatcg gggaaggatt ggcccgcgtt ggattagcta gttggtgggg taaaggccta     180
ccaaggcgac gatccatagc tggtctgaga ggatgatcag ccacattggg actgagacac     240
ggcccaaact cctacgggag gcagcagtgg ggaatattgg acaatgggcg caagcctgat     300
ccagccatgc cgcgtgagtg atgaaggcct tagggttgta aagctctttc accggagaag     360
ataatgacgg tatccggaga agaagccccg gctaacttcg tgccagcagc cgcggtaata     420
cgaagggggc tagcgttgtt cggaattact gggcgtaaag cgcacgtagg cggatattta     480
agtcaggggt gaaatcccag agctcaactc tggaactgcc tttgatactg ggtatcttga     540
gtatggaaga ggtaagtgga attccgagtg tagaggtgaa attcgtagat attcggagga     600
acaccagtgg cgaaggcggc ttactggtcc attactgacg ctgaggtgcg aaagcgtggg     660
```

```
gagcaaacag gattagatac cctggtagtc cacgccgtaa acgatgaatg ttagccgtcg      720
ggcagtatac tgttcggtgg cgcagctaac gcattaaaca ttccgcctgg ggagtacggt      780
cgcaagatta aaactcaaag gaattgacgg gggcccgcac aagcggtgga gcatgtggtt      840
taattcgaag caacgcgcag aaccttacca gctcttgaca ttcggggttt gggcagtgga      900
gacattgtcc ttcagttagg ctgggcccag aacaggtgct gcatggctgt cgtcagctcg      960
tgtcgtgaga tgttgggtta agtcccgcaa cgagcgcaac cctcgccctt agttgccagc     1020
atttagttgg gcactctaag gggactgccg gtgataagcc gagaggaagg tggggatgac     1080
gtcaagtcct catggccctt acgggctggg ctacacacgt gctacaatgg tggtgacagt     1140
gggcagcgag acagcgatgt cgagctaatc tccaaaagcc atctcagttc ggattgcact     1200
ctgcaactcg agtgcatgaa gttggaatcg ctagtaatcg cagatcagca tgctgcggtg     1260
aatacgttcc cgggccttgt acaccgcc cgtcacacca tgggagttgg ttttacccga      1320
aggtagtgcg ctaaccgcaa ggaggcagct atcca                                1355
```

<210> SEQ ID NO 2
<211> LENGTH: 1388
<212> TYPE: DNA
<213> ORGANISM: Pantoea sp.

<400> SEQUENCE: 2

```
ccatgcagtc ggacggtagc acagataagc ttgctccttg ggtgacgagt ggcggacggg       60
tgagtaatgt ctggggatct gcccgataga ggggataac cactgaaaac ggtggctaat      120
accgcataac gtcgcaagac caaagagggg gaccttcggg cctctcacta tcggatgaac      180
ccatatggga ttatctagta ggcggggtaa tggcccacct aggcgacgat ccctagctgg      240
tctgagagga tgaccagcca cactggaact gagacacggt ccagactcct acgggaggca      300
gcagtgggga atattgcaca atgggcgcaa gcctgatgca cccatgccgc gtgtatgaag      360
aaggccttcg ggttgtaaag tactttcagc ggggaggaag cgacggggt taataaccct      420 gtcgattgac gttacccgca gaagacgcac cggctaactc cgtgccagca gccgcggtaa      480 tacgagggt gcaagcgtta atcggaatta ctgggcgtaa agcgcacgca ggcggtctgt      540
taagtcacat gtgaaatccc ccgggcttaa cctgggaact gcatttgaaa ctggcaggct      600
tgagtcttgt agagggggt agaattcctg gtgtagcggt gaaatgcgta gagatctgga      660
cgaataccgg tggcgatcgc ggccccctgg acaaagactg acgctcacgt gcgaaagcgt      720
ggggagcaaa ctcgattaca taccctggta gtccacgccg taaacgatgt cgacttggag      780
gttgttccct tgaggagtgg cttccggagc taacgcgtta agtcgaccgc ctggggagta      840
cggccgcaag gttaaaactc aaatgaattg acggggccc gcacaagcgg tggagcatgt      900
ggtttaattc gatgcaacgc gaagaacctt acctactctt gacatccagc gaatttagca     960
gagatgcttt ggtgccttcg ggaacgctga gacaggtgct gcatggctgt cgtcagctcg    1020
tgttgtgaaa tgttgggtta agtcccgcaa cgagcgcaac ccttatcctt tgttgccagc    1080
gattcggtcg ggaactcaaa ggagactgcc ggtgataaac cggaggaagg tggggatgac    1140
gtcaagtcat catggccctt acgagtaggg ctacacacgt gctacaatgg cgcatacaaa    1200
gagaagcgac ctcgcgagag caagcggacc tcacaaagtg cgtcgtagtc cggatcggag    1260
tctgcaactc gactccgtga agtcggaatc gctagtaatc gtggatcaga atgccacggt    1320
gaatacgttc ccgggccttg tacaccgccc gtcacacacc atgggagtgg gttgcaaaag    1380
```

```
aagtagtt                                                                1388
```

<210> SEQ ID NO 3
<211> LENGTH: 1313
<212> TYPE: DNA
<213> ORGANISM: Sphingomonas sp.

<400> SEQUENCE: 3

```
catgcagtcg acgagccttt cggggctagt ggcgcacggg tgcgtaacgc gtgggaatct     60
gcccttgggt tcggaataac gtcgggaaac tgacgctaat accggatgat gacgtaagtc    120
caaagattta tcgcccaggg atgagcccgc gtaggattag ctagttggtg aggtaaaggc    180
tcaccaaggc gacgatcctt agctggtctg agaggatgat cagccacact gggactgaga    240
cacggcccag actcctacgg gaggcagcag tagggaatat tggacaatgg gggcaaccct    300
gatccagcaa tgccgcgtga gtgatgaagg ccttaggggtt gtaaagctct tttacccggg    360
atgataatga atacggaggg ggctagcgtt gttcggaatt actgggcgta aagcgcacgt    420
aggcggcgat ttaagtcaga ggtgaaagcc cggggctcaa ccccggaat agcctttgag     480
actggattgc ttgaacatcg agaggtgag tggaattccg agtgtagagg tgaaatttcg    540
tagatattcg gaagaacacc agtggcgaag gcggctcact ggacgattgt tgacgctgag    600
gtgcgaaagc gtgggagca acaggatta ataccctg gtagtccacg ccgtaaacga    660
tgataactag ctgctggggc tcatggagtt tcggtggcgc agctaacgca ttaagttatc    720
cgcctgggga gtacggtcgc aagattaaaa ctcaaaggaa ttgacggggg cctgcacaag    780
cggtggagca tgtggtttaa ttcgaagcaa cgcgcagaac cttaccaacg tttgacatcc    840
ctatcgcgga tcgtggagac actttccttc agttcggctg ataggtgac aggtgctgca     900
tggctgtcgt cagctcgtgt cgtgagaata cttgggttaa gtcccgcaac gagcgcaacc    960
ctcgccttta gttgccatca tttagttggg tactctaaag gaaccgccgg tgataagccg   1020
gaggaaggtg gggatgacgt caagtcctca tggcccttac gcgttgggct acacacgtgc   1080
tacaatggcg actacagtgg gcagccactc cgcgaggagg agctaatctc caaaagtcgt   1140
ctcagttcgg attgttctct gcaactcgag agcatgaagg cggaatcgct agtaatcgcg   1200
gatcagcatg ccgcggtgaa tacgttccca ggccttgtac acaccgcccg tcacaccatg   1260
ggagttggtt tcacccgaag gctgtgcgct aaccgcaagg aggcagcaga cca           1313
```

<210> SEQ ID NO 4
<211> LENGTH: 1422
<212> TYPE: DNA
<213> ORGANISM: Pseudomonas sp.

<400> SEQUENCE: 4

```
acacatgcag tcgagcggta gagaggtgct tgcacctctt gagagcggcg acgggtgag     60
taaagcctag gaatctgcct ggtagtgggg gataacgctc ggaaacggac gctaataccg    120
catacgtcct acgggagaaa gcaggggacc ttcgggcctt gcgctatcag atgagcctag    180
gtcggattag ctagttggtg aggtaatggc tcaccaaggc gacgatccgt aactggtctg    240
agaggatgat cagtcacact ggaactgaga cacggtccag actcctacgg gaggcagcag    300
tgggaatat tggacaatgg gcgaaagcct gatccagcca tgccgcgtgt gtgaagaagg    360
tcttcggatt gtaaagcact ttaagttggg aggaagggca ttaacctaat acgttagtgt    420
tttgacgtta ccgacagaat aagcaccggc taactctgtg ccagcagccg cggtaataca    480
gagggtgcaa gcgttaatcg gaattactgg gcgtaaagcg cgcgtaggtg gttcgttaag    540
```

```
ttggatgtga aatccccggg ctcaacctgg gaactgcatt caaaactgtc gagctagagt      600
atggtagagg gtggtggaat tcctgttgt agcggtgaaa tgcgtgatac agatatagga       660
aggaacacca gtggcgaagg cgacccacct ggactgatac tgacactgag gtgcgaaagc      720
gtggggagca aacaggatta gatacctgg gtagtccacg cccgtaaacg atgtcaacta      780
gccgttggga gccttgagct cttagtggcg cagctaacgc attaagttga ccgcctgggg      840
agtacggccg caaggttaaa actcaaatga attgacgggg gcccgcacaa gcggtggagc      900
atgtggttta attcgaagca acgcgaagta ccttaccagg ccttgacatc ctatgaactt      960
tccagagatg gattggtgcc ttcgggaaca ttgagacagg tgctgcatgg ctgtcgtcag     1020
ctcgtgtcgt gagatgttgg gttaagtccc gtaacgagcg caaccccttgt ccttagttac     1080 cagcacgtaa tggtgggcac tctaaggaga ctgccggtga caaaccggag gaaggtgggg     1140
atgacgtcaa gtcatcatgg cccttacggc ctgggctaca cacgtgctac aatggtcggt     1200
acagagggtt gccaagccgc gaggtggagc taatcccaca aaaccgatcg tagtccggat     1260
cgcagtctgc aactcgactg cgtgaagtcg gaatcgctag taatcgcgaa tcagaatgtc     1320
gcggtgaata cgttcccggg ccttgtacac accgcccgtc acaccatggg agtgggttgc     1380
accagaagta gctagtctaa ccttcggggg gacggtacca cg                         1422
```

<210> SEQ ID NO 5
<211> LENGTH: 1352
<212> TYPE: DNA
<213> ORGANISM: Enterobacter sp.

<400> SEQUENCE: 5

```
agtaatgtct gggaaactgc ctgatggagg gggataacta ctggaaacgg tagctaatac       60
cgcataacgt cgcaagacca agagggggga ccttcgggcc tcttgccatc agatgtgccc      120
agatgggatt agctagtagg tggggtaacg gctcacctag gcgacgatcc ctagctggtc      180
tgagaggatg accagccaca ctggaactga cacacggtcc agactcctac gggaggcagc      240
agtggggaat attgcacaat gggcgcaagc ctgatgcagc catgccgcgt gtatgaagaa      300
ggccttcggg ttgtaaagta ctttcagcgg ggaggaaggt gttgtggtta ataaccgcag      360
caattgacgt tacccgcaga agaagcaccg gctaactccg tgccagcagc cgcggtaata      420
cggagggtgc aagcgttaat cggaattact gggcgtaaag cgcacgcagg cggtctgtca      480
agtcggatgt gaaatccccg ggctcaacct gggaactgca ttcgaaactg caggctaga      540 gtcttgtaga gggggtaga attccaggtg tagcggtgaa atgcgtagag atctggagga      600
ataccggtgg cgaagggcgg ccccctggac aaagactgac gctcaggtgc gaaagcgtgg      660
ggagcaaaca ggattagata cccctggtag tccacgccgt aaacgatgtc gacttggagg      720
ttgtgccctt gaggcgtggc ttccggagct aacgcgttaa gtcgaccgcc tggggagtac      780
ggccgcaagg ataaaacctt aatgaattga cgggggcccg cacaagcggt ggagcatgtg      840
gtttaattcg atgcaacgcg aagaaccttt gctactcttg acatccagag aactttccag      900
agatggattg gtgccttcgg gaactctgag acaggtgctg catggctgtc gtcagctcgt      960
gttgtgaaat gttgggttaa gtcccgcaac gagcgcaacc cttatccttt gttgccagcg     1020
gtccggccgg gaactcaaag gagactgcca gtgataaact ggaggaaggt ggggatgacg     1080
tcaagtcatc atggccctta cgagtagggc tacacacgtg ctacaatggc gcatacaaag     1140
agaagcgaac tcgcgagagc aagcggacct cataaagtgc gtcgtagtcc ggattggagt     1200
```

| ctgcaactcg actccatgaa gtcggaatcg ctagtaatcg tagatcagaa tgctacggtg | 1260 |
| aatacgttcc cgggccttgt acacaccgcc cgtcacacca tgggagtggg ttgcaaaaga | 1320 |
| agtaggtagc ttaaccttcg ggagggcgct ac | 1352 |

```
<210> SEQ ID NO 6
<211> LENGTH: 1394
<212> TYPE: DNA
<213> ORGANISM: Micrococcus sp.

<400> SEQUENCE: 6
```

| gcatgcagtc gacgatgaag cccagcttgc tgggtggatt agtggcgaac gggtgagtaa | 60 |
| cacgtgagta acctgccctt aactctggga taagcctggg aaactgggtc taataccgga | 120 |
| tatgagcgcc taccgcatgg tgggtgttgg aaagatttat cggttttgga tggactcgcg | 180 |
| gcctatcagc ttgttggtga ggtaatggct caccaaggcg acgacgggta gccggcctga | 240 |
| gagggtgacc ggccacactg gactgagaca cggcccaga ctcctacggg aggcagcagt | 300 |
| ggggaatatt gcacaatggg cgaaagcctg atgcagcgac gccgcgtgag ggatgacggc | 360 |
| cttcgggttg taaacctctt tcagtaggga agaagcgaaa gtgacggtac ctgcagaaga | 420 |
| agcaccggct aactacgtgc cagcagccgc ggtaatacgt agggtgcgag cgttatccgg | 480 |
| aattattggg cgtaaagagc tcgtaggcgg tttgtcgcgt ctgtcgtgaa agtccggggc | 540 |
| ttaaccccgg atctgcggtg ggtacgggca gactagagtg cagtagggga gactggaatt | 600 |
| cctggtgtag cggtggaatg cgcagatatc aggaggaaca ccgatggcga aggcaggtct | 660 |
| ctgggctgta actgacgctg aggagcgaaa gcatggggag cgaacaggat tagatacect | 720 |
| ggtagtccat gccgtaaacg ttgggcacta gtgtgtggga ccattccacg gtttccgcgc | 780 |
| cgcagctaac gcattaagtg ccccgcctgg ggagtacggc cgcaaggcta aaactcaaag | 840 |
| gaattgacgg gggcccgcac aagcggcgga gcatgcggat taattcgatg caacgcgaag | 900 |
| tagcttacca aggcttgaca tgtactcgat cggcgtagag atacggtttc ccgttagggg | 960 |
| cgggttctgt ggtggtgcat ggttgtcgtc agctcgtgtc gtgagatgtt gggttaagtc | 1020 |
| ccgcaacgag cgcaaccctc gttccatgtt gccagcacgt cgtggtgggg actcatggga | 1080 |
| gactgccggg gtcaactcgg aggaaggtga ggacgacgtc aaatcatcat gccccttatg | 1140 |
| tcttgggctt cacgcatgct acaatggccg gtacaatggg ttgcgatact gtgaggtgga | 1200 |
| gctaatccca aaaagccggt ctcagttcgg attggggtct gcaactcgac cccatgaagt | 1260 |
| cggagtcgct agtaatcgca gatcagcaac gctgcggtga atacgttccc gggccttgta | 1320 |
| cacaccgccc gtcaagtcac gaaagttggt aacacccgaa gccggtggcc taaccettgt | 1380 |
| gggggagcc gtac | 1394 |

```
<210> SEQ ID NO 7
<211> LENGTH: 1421
<212> TYPE: DNA
<213> ORGANISM: Bacillus sp.

<400> SEQUENCE: 7
```

| atgcagtcga gcgaatcgat gggagcttgc tccctgagat tagcggcgga cgggtgagta | 60 |
| acacgtgggc aacctgccta taagactggg ataacttcgg gaaaccggag ctaataccgg | 120 |
| atacgttctt ttctcgcatg agagaagatg gaaagacggt ttacgctgtc acttatagat | 180 |
| gggcccgcgg cgcattagct agttggtgag gtaatggctc accaaggcga cgatgcgtag | 240 |
| ccgacctgag agggtgatcg gccacactgg gactgagaca cggcccagac tcctacggga | 300 |

```
ggcagcagta gggaatcttc cgcaatggac gaaagtctga cggagcaacg ccgcgtgaac    360
gaagaaggcc ttcgggtcgt aaagttctgt tgttagggaa gaacaagtac cagagtaact    420
gctggtacct tgacggtacc taaccagaaa gccacggcta actacgtgcc agcagccgcg    480
gtaatacgta ggtggcaagc gttgtccgga attattgggc gtaaagcgcg cgcaggtggt    540
tccttaagtc tgatgtgaaa gcccacggct caaccgtgga gggtcattgg aaactgggga    600
acttgagtgc agaagaggaa agtggaattt ccaagtgtag cggtgaaatg cgtagagatt    660
tggaggaaca ccagtggcga aggcgacttt ctggtctgta actgacactg aggcgcgaaa    720
gcgtggggag caaacaggat tagataccct ggtagtccac gccgtaaacg atgagtgcta    780
agtgttagag ggtttccgcc ctttagtgct gcagctaacg cattaagcac tccgcctggg    840
gagtacggcc gcaaggctga aactcaaagg aattgacggg ggcccgcaca agcggtggag    900
catgtggttt aattcgaacg atcccgttct accttaccag gtgatgacat cctctgacaa    960
ccctagagat agggctttcc ccttcggggg acagagtgac aggtggtgca tggttgtcgt   1020
cagctcgtgt cgtgagatgt tgggttaagt cccgcaacga gcgcaaccct tgatcttagt   1080
tgccagcatt cagttgggca ctctaaggtg actgccggtg acaaaccgga ggaaggtggg   1140
gatgacgtca atcatcatg ccccttatga cctgggctac acacgtgcta caatggatgg   1200
tacaaagggc tgcaaacctg cgaaggtaag cgaatcccat aaagccattc tcagttcgga   1260
ttgcaggctg caactcgcct gcatgaagcc ggaatcgcta gtaatcgcgg atcagcatgc   1320
cgcggtgaat acgttcccgg gccttgtaca caccgcccgt cacaccacga gagtttgtaa   1380 caccgaagt cggtgaggta accttcatgg agccagccgc c                        1421
```

<210> SEQ ID NO 8
<211> LENGTH: 1419
<212> TYPE: DNA
<213> ORGANISM: Pantoea sp.

<400> SEQUENCE: 8

```
ccatgcagtc ggacggtagc acagaggagc ttgctcctcg ggtgacgagt ggcggacggg     60
tgagtaatgt ctgggatct gcccgataga ggggataac cactggaaac ggtggctaat    120
accgcaaaac gtcgcaagac caaagagggg gaccttcggg cctctcacta tcggatgaac    180
ccagatggga ttagctagta ggcggggtaa cggcccacct aggcgacgat ccctagctgg    240
tctgagagga tgaccagcca cactggaact gagacacggt ccagactcct acgggaggca    300
gcagtgggga atattgcaca atgggcgcaa gcctgatgca gccatgccgc gtgtatgaag    360
aaggccttcg ggttgtaaag tactttcagc ggggaggaag gcgatgtggt taataaccgc    420
gtcgattgac gttacccgca gaagaagcac cggctaactc cgtgccagca gccgcggtaa    480
tacggagggt gcaagcgtta atcggaatta ctgggcgtaa agcgcacgca ggcggtctgt    540
taagtcagat gtgaaatccc cgggcttaac ctgggaactg catttgaaac tggcaggctt    600
gagtctcgta gaggggggta gaatttccag gtgtagcggt gaaatgcgta gagatctgga    660
ggaataccgg tggcgaaggc ggccccctgg acgaagactg acgctcaggt gcgaaagcgt    720
ggggagcaaa caggattaga taccctggta gtccacgccg taaacgatgt cgacttggag    780
gttgttccct tgaggagtgg cttccggagc taacgcgtta agtcgaccgc ctggggagta    840
cggccgcaag gattaaactc aaatgaattg acggggcccc gcacaagcgg tggagcatgt    900
ggtttaattc gatgcaacgc gaagaaccat acctactctt gacatccaga gaacttagca    960
```

-continued

```
gagatgcttt ggtgccttcg ggaactctga cacaggtgct gcatggctgt cgtcagctcg      1020
tgttgtgaaa tgttgggtta agtcccgcaa cgagcgcaac ccttatcctt tgttgccagc      1080
gattcggtcg ggaactcaaa ggagactgcc ggtgataaac cggaggaagg tggggatgac      1140
gtcaagtcat catggccctt acgagtaggg ctacacacgt gctacaatgg cgcatacaaa      1200
gagaagcgac ctcgcgagag caagcggacc tcataaagtg cgtcgtagtc cggatcggag      1260
tctgcaactc gactccgtga agtcggaatc gctagtaatc gtggatcaga atgccacggt      1320
gaatacgttc ccgggccttg tacacaccgc ccgtcacacc atgggagtgg gttgcaaaag      1380
aagtaggcta gcttaacctt cgggagggcg ctaccactt                            1419
```

<210> SEQ ID NO 9
<211> LENGTH: 1420
<212> TYPE: DNA
<213> ORGANISM: Actinobacter sp.

<400> SEQUENCE: 9

```
cacatgcagt cgagcgggga gagtagcttg ctacttgacc tagcggcgga cgggtgagta       60
atgcttagga atctgcctat tagtgggga caacatctcg aaagggatgc taataccgca      120
tacgtcctac gggagaaagc aggggacctt cgggccttgc gctaatagat gagcctaagt      180
cggattagct agttggtggg gtaaaggcct accaaggcga cgatctgtag cgggtctgag      240
aggatgatcc gccacactgg gactgagaca cggcccagac tcctacggga ggcagcagtg      300
gggaatattg gacaatgggg gaaccctga tccagccatg ccgcgtgtgt gaagaaggcc      360
ttttggttgt aaagcacttt aagcgaggag gaggctaccg agattaatac tcttggatag      420
tggacgttac tcgcagaata agcaccggct aactctgtgc cagcagccgc ggtaatacag      480
agggtgcaag cgttaatcgg atttactggg cgtaaagcgc gcgtaggtgg ccaattaagt      540
caaatgtgaa atccccgagc ttaacttggg aattgcattc gatactggtt ggctagagta      600
tgggagagga tggtagaatt ccaggtgtag cggtgaaatg cgtagagatc tggaggaata      660
ccgatggcga aggcagccat ctggcctaat actgacactg aggtgcgaaa gcatggggag      720
caaacaggat tagataccct ggtagtccat gccgtaaacg atgtctacta gccgttgggg      780
cctttgctgg ctttagtggc gcagctaacg cgataagtag accgcctggg gagtacggtc      840
gcaagactaa aactcaaatg aattgacggg ggcccgcaca agcggtggag catgtggttt      900
aattcgatgc aacgcgaagt agcttacctg gtcttgacat agtatcttct ttccagagat      960
ggattggtgc cttcgggaac ttacatacag gtgctgcatg gctgtcgtca gctcgtgtcg     1020
tgagatgttg ggttaagtcc cgcaacgagc gcaacccttt tccttatttg ccagcgggtt     1080
aagccgggaa ctttaaggat actgccagtg acaaactgga ggaaggcggg gacgacgtca     1140
agtcatcatg gcccttacga ccagggctac acacgtgcta caatggtcgg tacaaagggt     1200
tgctacctcg cgagaggatg ctaatctcaa aaagccgatc gtagtccgga ttggagtctg     1260
caactcgact ccatgaagtc ggaatcgcta gtaatcgcgg atcagaatgc cgcggtgaat     1320
acgttcccgg gccttgtaca caccgcccgt cacaccatgg gagtttgttg caccagaagt     1380
agggtaggtc cttaacgtct aagggaggac gctaccacgg                            1420
```

<210> SEQ ID NO 10
<211> LENGTH: 1436
<212> TYPE: DNA
<213> ORGANISM: Paenibacillus sp.

<400> SEQUENCE: 10

-continued

```
atacatgcag tcgagcggac ttgcatgaga agcttgcttc tctgatggtt agcggcggac        60
gggtgagtaa cacgtaggca cctgccctca agcttgggac aactaccgga aacggtagct       120
aataccgaat agttgttttc ttctcctgaa gaaaactgga aagacggagc aatctgtcac       180
ttggggatgg gcctgcggcg cattagctag ttggtggggt aacggctcac caaggcgacg       240
atgcgtagcc gacctgagag ggtgatcggc cacactggga ctgagacacg gcccagactc       300
ctacgggagg cagcagtagg gaatcttccg caatgggcga agcctgacg gagcaatgcc        360 gcgtgagtga tgaaggtttt cggatcgtaa agctctgttg ccagggaaga acgcttggga       420
gagtaactgc tctcaaggtg acggtacctg agaagaaagc cccggctaac tacgtgccag       480
cagccgcggt aatacgtagg gggcaagcgt tgtccggaat tattgggcgt aaagcgcgcg       540
caggcggtca tttaagtctg gtgtttaatc ccggggctca accccggatc gcactggaaa       600
ctgggtgact tgagtgcaga agaggagagt ggaattccac gtgtagcggt gaaatgcgta       660
gatatgtgga ggaacaccag tggcgaagcg cgactctctg ggctgtaact gacgctgagg       720
cgcgaaagcg tggggagcaa acaggattag ataccctggt agtccacgcc gtaaacgatg       780
agtgctaggt gttaggggtt tcgatacccct tggtgccgaa gttaacacat taagcactcc      840
gcctggggag tacggtcgca agactgaaac tcaaaggaat tgacggggac ccgcacaagc       900
agtggagtat gtggttttat tcgaagcaac gcgaagaacc ttaccaggtc ttgacatccc       960
tctgaccggt acagagatgt acctttcctt cgggacagag gagacaggtg gtgcatggtt      1020
gtcgtcagct cgtgtcgtga gatgttgggt taagtcccgc aacgagcgca acccttgatc      1080
ttagttgcca gcacttcggg tgggcactct aaggtgactg ccggtgacaa accggaggaa      1140
ggtggggatg acgtcaaatc atcatgcccc ttatgacctg ggctacacac gtactacaat      1200
ggccggtaca acgggctgtg aagccgcgag gtggaacgaa tcctaaaaag ccggtctcag      1260
ttcggattgc aggctgcaac tcgcctgcat gaagtcggaa ttgctagtaa tcgcggatca      1320
gcatgccgcg gtgaatacgt tcccgggtct tgtacacacc gcccgtcaca ccacgagagt      1380
ttataacacc cgaagtcggt ggggtaaccg caaggagcca gccgccgaag gtgatc         1436
```

PLANT-ENDOPHYTE COMBINATIONS AND USES THEREFOR

BACKGROUND

With limited arable land coupled with rising demand of a steadily increasing human population that could reach 9 billion by 2050, food supply is a global challenge making production of economically attractive and high quality food, free from unacceptable levels of agrochemicals, a dire need.

Traditional plant breeding strategies to enhance plant traits are relatively slow and inefficient. For example, breeding plants for increased tolerance to abiotic stress requires abiotic stress-tolerant founder lines for crossing with other germplasm to develop new abiotic stress-resistant lines. Limited germplasm resources for such founder lines and incompatibility in crosses between distantly related plant species represent significant problems encountered in conventional breeding. Breeding for stress tolerance has often been inadequate given the incidence of stresses and the impact that stresses have on crop yields in most environments of the world.

SUMMARY OF THE INVENTION

The present invention is based on the systematic efforts to discover endophytic bacterial species that have the potential to greatly improve agricultural productivity. The endophytic bacterial strains extensively characterized herein are able to confer onto the host plant several key fitness benefits and, as such, offer the possibility of improving yields of agricultural crops without the need for time-consuming breeding efforts or genetic modification.

In a first aspect, the present invention provides for an agricultural plant or portion thereof comprising an exogenous endophytic bacterial population disposed on an exterior surface of the seed or seedling in an amount effective to colonize the plant, and further comprising a formulation that comprises at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient. The agricultural plant can be a mature plant. In other cases, it can be a seedling. In still other cases, it can be a seed of an agricultural plant. In one particular embodiment, the agricultural plant is a seed or seedling.

In one embodiment, the endophytic bacterial population consists essentially of an endophytic bacterium comprising a 16S rRNA nucleic acid sequence at least 97% identical to a nucleic acid sequence selected from the group consisting of SEQ ID NOs: 1-10.

In one particular embodiment, the endophytic bacterium is a species of *Agrobacterium*. In a particular embodiment, the *Agrobacterium* species is identified on the basis of its rDNA sequence, as outlined herein. In a particular embodiment, the *Agrobacterium* species comprises a 16S rDNA sequence that is at least 97% identical to SEQ ID NO: 1. In another embodiment, the *Agrobacterium* species comprises a 16S rDNA sequence that is at least 99% identical to SEQ ID NO: 1. In still another embodiment, the *Agrobacterium* species comprises a 16S rDNA sequence that is identical to SEQ ID NO: 1. In still another embodiment, the *Agrobacterium* species is the isolate FA13.

In another embodiment, the endophytic bacterium is a species of *Pantoea*. In a particular embodiment, the *Pantoea* species is identified on the basis of its rDNA sequence, as outlined herein. In a particular embodiment, the *Pantoea* species comprises a 16S rDNA sequence that is at least 97% identical to SEQ ID NO: 2. In another embodiment, the *Pantoea* species comprises a 16S rDNA sequence that is at least 99% identical to SEQ ID NO: 2. In still another embodiment, the *Pantoea* species comprises a 16S rDNA sequence that is identical to SEQ ID NO: 2. In still another embodiment, the *Pantoea* species is the isolate FF34.

In another embodiment, the endophytic bacterium is a species of *Sphingobium*. In a particular embodiment, the *Sphingobium* species is identified on the basis of its rDNA sequence, as outlined herein. In a particular embodiment, the *Sphingobium* species comprises a 16S rDNA sequence that is at least 97% identical to SEQ ID NO: 3. In another embodiment, the *Sphingobium* species comprises a 16S rDNA sequence that is at least 99% identical to SEQ ID NO: 3. In still another embodiment, the *Sphingobium* species comprises a 16S rDNA sequence that is identical to SEQ ID NO: 3. In still another embodiment, the *Sphingobium* species is the isolate FC42.

In another embodiment, the endophytic bacterium is a species of *Pseudomonas*. In a particular embodiment, the *Pseudomonas* species is identified on the basis of its rDNA sequence, as outlined herein. In a particular embodiment, the *Pseudomonas* species comprises a 16S rDNA sequence that is at least 97% identical to SEQ ID NO: 4. In another embodiment, the *Pseudomonas* species comprises a 16S rDNA sequence that is at least 99% identical to SEQ ID NO: 4. In still another embodiment, the *Pseudomonas* species comprises a 16S rDNA sequence that is identical to SEQ ID NO: 4. In still another embodiment, the *Pseudomonas* species is the isolate FB12.

In another embodiment, the endophytic bacterium is a species of *Enterobacter*. In a particular embodiment, the *Enterobacter* species is identified on the basis of its rDNA sequence, as outlined herein. In a particular embodiment, the *Enterobacter* species comprises a 16S rDNA sequence that is at least 97% identical to SEQ ID NO: 5. In another embodiment, the *Enterobacter* species comprises a 16S rDNA sequence that is at least 99% identical to SEQ ID NO: 5. In still another embodiment, the *Enterobacter* species comprises a 16S rDNA sequence that is identical to SEQ ID NO: 5. In still another embodiment, the *Enterobacter* species is the isolate FD17.

In another embodiment, the endophytic bacterium is a species of *Micrococcus*. In a particular embodiment, the *Micrococcus* species is identified on the basis of its rDNA sequence, as outlined herein. In a particular embodiment, the *Micrococcus* species comprises a 16S rDNA sequence that is at least 97% identical to SEQ ID NO: 6. In another embodiment, the *Micrococcus* species comprises a 16S rDNA sequence that is at least 99% identical to SEQ ID NO: 6. In still another embodiment, the *Micrococcus* species comprises a 16S rDNA sequence that is identical to SEQ ID NO: 6. In still another embodiment, the *Micrococcus* species is the isolate S2.

In another embodiment, the endophytic bacterium is a species of *Bacillus*. In a particular embodiment, the *Bacillus* species is identified on the basis of its rDNA sequence, as outlined herein. In a particular embodiment, the *Bacillus* species comprises a 16S rDNA sequence that is at least 97% identical to SEQ ID NO: 7. In another embodiment, the *Bacillus* species comprises a 16S rDNA sequence that is at least 99% identical to SEQ ID NO: 7. In still another embodiment, the *Bacillus* species comprises a 16S rDNA sequence that is identical to SEQ ID NO: 7. In still another embodiment, the *Bacillus* species is the isolate S4.

In another embodiment, the endophytic bacterium is a species of *Pantoea*. In a particular embodiment, the *Pantoea* species is identified on the basis of its rDNA sequence, as outlined herein. In a particular embodiment, the *Pantoea* species comprises a 16S rDNA sequence that is at least 97% identical to SEQ ID NO: 8. In another embodiment, the *Pantoea* species comprises a 16S rDNA sequence that is at least 99% identical to SEQ ID NO: 8. In still another embodiment, the *Pantoea* species comprises a 16S rDNA sequence that is identical to SEQ ID NO: 8. In still another embodiment, the *Pantoea* species is the isolate S6.

In another embodiment, the endophytic bacterium is a species of *Acinetibacter*. In a particular embodiment, the *Acinetobacter* species is identified on the basis of its rDNA sequence, as outlined herein. In a particular embodiment, the *Acinetobacter* species comprises a 16S rDNA sequence that is at least 97% identical to SEQ ID NO: 9. In another embodiment, the *Acinetobacter* species comprises a 16S rDNA sequence that is at least 99% identical to SEQ ID NO: 9. In still another embodiment, the *Acinetobacter* species comprises a 16S rDNA sequence that is identical to SEQ ID NO: 9. In still another embodiment, the *Acinetobacter* species is the isolate S9.

In another embodiment, the endophytic bacterium is a species of *Paenibacillus*. In a particular embodiment, the *Paenibacillus* species is identified on the basis of its rDNA sequence, as outlined herein. In a particular embodiment, the *Paenibacillus* species comprises a 16S rDNA sequence that is at least 97% identical to SEQ ID NO: 10. In another embodiment, the *Paenibacillus* species comprises a 16S rDNA sequence that is at least 99% identical to SEQ ID NO: 10. In still another embodiment, the *Paenibacillus* species comprises a 16S rDNA sequence that is identical to SEQ ID NO: 10. In still another embodiment, the *Paenibacillus* species is the isolate S10.

In certain cases, the endophytic bacterial population is disposed in an amount effective to be detectable within a target tissue of the mature agricultural plant selected from a fruit, a seed, a leaf, or a root, or portion thereof.

In certain embodiments, the seed or seedling comprises at least about 100 CFU, for example, at least about 200 CFU, at least about 300 CFU, at least about 500 CFU, at least about 1,000 CFU, at least about 3,000 CFU, at least about 10,000 CFU, at least about 30,000 CFU, at least about 100,000 CFU or more, of the endophytic bacterial population on its exterior surface.

In another embodiment, the endophytic bacterial population is disposed on an exterior surface or within a tissue of the seed or seedling in an amount effective to be detectable in an amount of at least about 100 CFU, for example, at least about 200 CFU, at least about 300 CFU, at least about 500 CFU, at least about 1,000 CFU, at least about 3,000 CFU, at least about 10,000 CFU, at least about 30,000 CFU, at least about 100,000 CFU or more per gram fresh weight of the mature agricultural plant.

In another embodiment, the endophytic bacterial population is disposed on the surface or within a tissue of the seed or seedling in an amount effective to increase the biomass of the fruit or cob from the resulting plant by at least 10% when compared with a reference agricultural plant.

In still another embodiment, the endophytic bacterial population is disposed on the surface or within a tissue of the seed or seedling in an amount effective to detectably colonize the soil environment surrounding the mature agricultural plant when compared with a reference agricultural plant.

In some cases, the endophytic bacterial population is disposed in an amount effective to increase root biomass by at least 10% when compared with a reference agricultural plant.

In some embodiments, the endophytic bacterial population is disposed on the surface or within a tissue of the seed or seedling in an amount effective to increase the rate of seed germination when compared with a reference agricultural plant.

In another embodiment, the endophytic bacterial population is disposed on the surface or within a tissue of the seed or seedling in an amount effective to detectably induce production of auxin in the seed or seedling.

In one embodiment, the endophytic bacterial population is cultured prior to disposition on the seed or seedling. In one embodiment, the endophytic bacterial population is cultured in a synthetic or semi-synthetic medium prior to disposition on the seed or seedling.

In certain cases, the endophytic bacterial population can be modified. In one embodiment, the endophytic bacterial population is genetically modified. In another embodiment, the endophytic bacterial population is modified such that it has enhanced compatibility with an antimicrobial agent when compared with an unmodified control. The antimicrobial agent is an antibacterial agent. Alternatively, the antimicrobial agent can be an antifungal agent. In some cases, the modified endophytic bacterial population exhibits at least 3 fold greater, for example, at least 5 fold greater, at least 10 fold greater, at least 20 fold greater, at least 30 fold greater or more resistance to the antimicrobial agent when compared with an unmodified control. In one embodiment, the antimicrobial agent is glyphosate.

The seed or seedling of the agricultural plant can be a monocot. For example, it can be a corn seed or seedling. Alternatively, it can be a wheat seed or seedling. In other embodiments, it can be a barley seed or seedling. In still other cases, it can be a rice seed or seedling.

In another embodiment, the seed or seedling is a dicot. For example, it can be a cotton seed or seedling, a soy seed or seedling, or a tomato seed or seedling.

In still another embodiment, the seed or seedling can be derived from a transgenic plant. In another embodiment, the seed or seedling can be a hybrid seed or seedling.

In one particular embodiment, the seed is a corn seed, and further comprises at least about 10,000 CFU of the endophytic bacterial population consisting essentially of an endophytic bacterium comprising a 16S rRNA nucleic acid sequence that is at least 97%, for example, at least 99%, at least 99.5%, or 100% identical to a nucleic acid sequence selected from the group consisting of [SEQ ID NOs: 1-10] disposed on the exterior surface of the seed, and further comprising a formulation comprising a microbial stabilizer.

In another aspect, the invention provides for a substantially uniform population of seeds comprising a plurality of seeds described above. Substantial uniformity can be determined in many ways. In some cases, at least 10%, for example, at least 20%, at least 30%, at least 40%, at least 50%, at least 60%, at least 70%, at least 75%, at least 80%, at least 90%, at least 95% or more of the seeds in the population, contains the endophytic bacterial population in an amount effective to colonize the plant disposed on the surface of the seeds. In other cases, at least 10%, for example, at least 20%, at least 30%, at least 40%, at least 50%, at least 60%, at least 70%, at least 75%, at least 80%, at least 90%, at least 95% or more of the seeds in the population, contains at least 100 CFU on its surface, for example, at least 200 CFU, at least 300 CFU, at least 1,000 CFU, at least 3,000 CFU, at least 10,000 CFU, at least 30,000 CFU, at least 100,000 CFU, at least 300,000 CFU, or at least 1,000,000 CFU per seed or more.

In yet another aspect, the present invention provides for a bag comprising at least 1,000 seeds as described herein above. The bag further comprises a label describing the seeds and/or said endophytic bacterial population.

In still another aspect of the present invention, a plant or part or tissue of the plant, or progeny thereof is disclosed, which is generated by growing the seed or seedling described herein above.

In yet another aspect, disclosed are substantially uniform populations of plants produced by growing a plurality of seeds, seedlings, or progeny thereof. In some cases, at least 75%, at least 80%, at least 90%, at least 95% or more of the plants in the population comprise an amount of the endophytic bacterial population effective to increase the root biomass of the plant by at least 10%. In other cases, at least 10%, for example at least 20%, at least 30%, at least 40%, at least 50%, at least 60%, at least 70%, at least 75%, at least 80%, at least 90%, at least 95% or more of the plants comprise a microbe population that is substantially similar.

In yet another aspect of the present invention, disclosed is an agricultural field comprising the population described above. The field generally comprises at least 100 plants, for example, at least 1,000 plants, at least 3,000 plants, at least 10,000 plants, at least 30,000 plants, at least 100,000 plants or more in the field. In certain cases, the population of plants occupies at least about 100 square feet of space, and at least about 10%, for example, at least 20%, at least 30%, at least 40%, at least 50%, at least 60%, at least 70%, at least 80%, at least 90% or more than 90% of the population comprises an amount of the endophytic bacterial population effective to increase the root biomass of the plant by at least 10%. In another embodiment, the population of plants occupies at least about 100 square feet of space, wherein and at least about 10%, for example, at least 20%, at least 30%, at least 40%, at least 50%, at least 60%, at least 70%, at least 80%, at least 90% or more than 90% of the population comprises the microbe in reproductive tissue. In another embodiment, the population of plants occupies at least about 100 square feet of space, and at least about 10%, for example, at least 20%, at least 30%, at least 40%, at least 50%, at least 60%, at least 70%, at least 80%, at least 90% or more than 90% of the population comprises at least 100 CFUs, 1,000 CFUs, 10,000 CFUs, 100,000 CFUs or more of the endophytic bacterial population.

In another aspect of the invention, provided are preparations comprising a population of endophytic bacteria described herein and further comprising at least one agent selected from the group consisting of an agriculturally acceptable carrier, a tackifier, a microbial stabilizer, a fungicide, an antibacterial agent, an herbicide, a nematicide, an insecticide, a plant growth regulator, a rodenticide, and a nutrient, and wherein the population comprises an amount of endophytes sufficient to improve an agronomic trait of the population of seeds. In one embodiment, the endophytic bacterial population consists essentially of an endophytic bacterium comprising a 16S rRNA nucleic acid sequence at least 97% identical to a nucleic acid sequence selected from the group consisting of SEQ ID NOs: 1-10.

In one embodiment, the preparation is substantially stable at temperatures between about 4° C. and about 45° C. for at least about seven days.

In another embodiment, the preparation is formulated to provide at least 100 endophytes per seed, for example, at least 300 endophytes, at least 1,000 endophytes, at least 3,000 endophytes, at least 10,000 endophytes, at least 30,000 endophytes, at least 100,000 endophytes, at least 300,000 endophytes, or at least 1,000,000 endophytes per seed.

In another embodiment, the preparation is formulated to provide a population of plants that demonstrates a substantially homogenous growth rate when introduced into agricultural production.

In still another aspect, the present invention provides for a method of producing a commodity plant product. The method generally comprises obtaining a plant or plant tissue from the agricultural plant comprising the endophytic bacteria as described herein above, and producing the commodity plant product therefrom. In certain cases, the commodity plant product is selected from the group consisting of grain, flour, starch, seed oil, syrup, meal, flour, oil, film, packaging, nutraceutical product, an animal feed, a fish fodder, a cereal product, a processed human-food product, a sugar or an alcohol and protein.

In a related aspect, the present invention provides for a commodity plant product comprising a plant or part thereof and further comprising the endophytic bacterial population or a portion thereof in a detectable level.

In yet another aspect of the present invention, provided is a method for preparing an agricultural plant or a portion thereof comprising an endophytic bacterial population. The method generally comprises applying to the seed or seedling a formulation comprising an endophytic bacterial population consisting essentially of an endophytic bacterium comprising a 16S rRNA nucleic acid sequence at least 97% identical, for example, at least 98% identical, at least 99% identical, at least 99.5% identical, or 100% identical to a nucleic acid sequence selected from the group consisting of [SEQ ID NOs: 1-10]. In one embodiment, the formulation further comprises at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient. In some cases, the agricultural plant can be a seedling. In other cases, the agricultural plant can be a seed. In a particular embodiment, the agricultural plant is a seed or a seedling. In another embodiment, the method further comprises applying at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient.

In a final aspect, the present invention provides for a method for conferring one or more fitness benefits to an agricultural plant. The method generally comprises providing an agricultural plant or portion thereof, contacting said plant or portion thereof with a formulation comprising an exogenous endophytic bacterial population consisting essentially of an endophytic bacterium comprising a 16S rRNA nucleic acid sequence at least 97% identical, for example, at least 98% identical, at least 99% identical, at least 99.5% identical, or 100% identical to a nucleic acid sequence selected from the group consisting of [SEQ ID NOs: 1-10], disposed on an exterior surface in an amount effective to colonize the mature plant, wherein the formulation further comprises at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient, and allowing the seed or seedling to grow under conditions that allow the endophytic bacterium to colonize the plant. In some cases, the agricultural plant can be a seedling. In other cases, the agricultural plant can be a seed. In a particular embodiment, the agricultural plant is a seed or a seedling.

In one embodiment, the one or more of the fitness benefits are selected from the group consisting of increased germination, increased biomass, increased flowering time, increased biomass of the fruit or grain, increased grain or fruit yield, and increased drought tolerance.

DETAILED DESCRIPTION

Brief Description of the Figures

FIG. 1A, FIG. 1B, and FIG. 1C each show the increases in root and shoot length in maize plants inoculated with the bacterial endophyte populations when compared with uninoculated control plants.

DEFINITIONS

Figure 2:
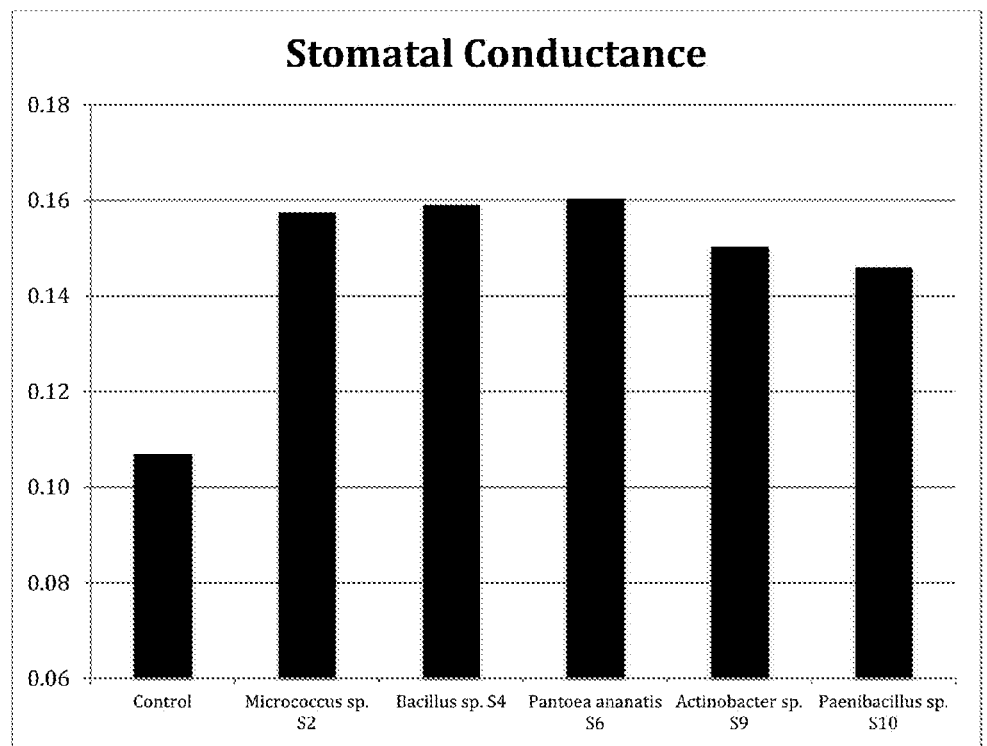
FIG. 2 shows the increases in stomatal conductance in maize plants inoculated with the bacterial endophyte populations when compared with uninoculated control plants.

A "synthetic combination" includes a combination of a host plant and an endophyte. The combination may be achieved, for example, by coating the surface of the seed of a plant, such as an agricultural plant, or host plant tissues with an endophyte.

As used herein, an "agricultural seed" is a seed used to grow a plant in agriculture (an "agricultural plant"). The seed may be of a monocot or dicot plant, and is planted for the production of an agricultural product, for example grain, food, fiber, etc. As used herein, an agricultural seed is a seed that is prepared for planting, for example, in farms for growing.

An "endophyte", or "endophytic microbe" includes an organism capable of living within a plant or associated therewith. An endophyte may refer to a bacterial or fungal organism that may confer an increase in yield, biomass, resistance, or fitness in its host plant. Endophytes may occupy the intracellular or extracellular spaces of plant tissue, including the leaves, stems, flowers, fruits, seeds, or roots. An endophyte can be a fungus, or a bacterium. As used herein, the term "microbe" is sometimes used to describe an endophyte.

In some embodiments, the invention contemplates the use of microbes that are "exogenous" to a seed or plant. As used herein, a microbe is considered exogenous to the seed or plant if the seed or seedling that is unmodified (e.g., a seed or seedling that is not treated with the endophytic bacterial population descried herein) does not contain the microbe.

In other cases, the invention contemplates the synthetic combinations of agricultural plants and an endophytic microbe population, in which the microbe population is "heterologously disposed" on the surface of or within a tissue of the agricultural plant. As used herein, a microbe is considered "heterologously disposed" on the surface or within a plant (or tissue) when the microbe is applied or disposed on the plant in a number or within a tissue in a number that is not found on that plant prior to application of the microbe. As such, a microbe is deemed heterologously disposed when applied on the plant that either does not naturally have the microbe on its surface or within the particular tissue to which the microbe is disposed, or does not naturally have the microbe on its surface or within the particular tissue in the number that is being applied. For the avoidance of doubt, "heterologously disposed" contemplates use of microbes that are "exogenous" to a seed or plant.

In some cases, the present invention contemplates the use of microbes that are "compatible" with agricultural chemicals for example, a fungicide, an anti-bacterial compound, or any other agent widely used in agricultural which has the effect of interfering with optimal growth of microbes. As used herein, a microbe is "compatible" with an agricultural chemical, when the microbe is modified or otherwise adapted to grow in, or otherwise survive, the concentration of the agricultural chemical used in agriculture. For example, a microbe disposed on the surface of a seed is compatible with the fungicide metalaxyl if it is able to survive the concentrations that are applied on the seed surface.

"Biomass" means the total mass or weight (fresh or dry), at a given time, of a plant tissue, plant tissues, an entire plant, or population of plants, usually given as weight per unit area. The term may also refer to all the plants or species in the community (community biomass).

Some of the compositions and methods described herein involve endophytic microbes in an amount effective to colonize a plant. As used herein, a microbe is said to "colonize" a plant or seed when it can exist in an endophytic relationship with the plant in the plant environment, for example inside the plant or a part or tissue thereof, including the seed.

Some compositions described herein contemplate the use of an agriculturally compatible carrier. As used herein an "agriculturally compatible carrier" is intended to refer to any material, other than water, which can be added to a seed or a seedling without causing/having an adverse effect on the seed, the plant that grows from the seed, seed germination, or the like.

A "transgenic plant" includes a plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences that are native to the plant being transformed, but wherein the "exogenous" gene has been altered in order to alter the level or pattern of expression of the gene, for example, by use of one or more heterologous regulatory or other elements.

As used herein, a nucleic acid has "homology" or is "homologous" to a second nucleic acid if the nucleic acid sequence has a similar sequence to the second nucleic acid sequence. The terms "identity", "percent sequence identity" or "identical" in the context of nucleic acid sequences refer to the residues in the two sequences that are the same when aligned for maximum correspondence. There are a number of different algorithms known in the art that can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990). The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, or at least about 90%, or at least about 95%, 96%, 97%, 98% or 99% of the nucleotide bases, as measured by any well-known algorithm of sequence identity, such as FASTA, BLAST or Gap, as discussed above.

The present invention is directed to methods and compositions of bacterial endophytes, and plant-endophyte combinations that confer a fitness benefit in agricultural plants.

Bacterial Endophyte

In a first aspect, disclosed is a composition comprising a pure culture of a bacterial endophyte.

In one embodiment, the endophytic bacterium is a species of *Agrobacterium*. In a particular embodiment, the *Agrobacterium* species is identified on the basis of its rDNA sequence, as outlined herein. In a particular embodiment, the *Agrobacterium* species comprises a 16S rDNA sequence that is at least 97% identical to SEQ ID NO: 1. In another embodiment, the *Agrobacterium* species comprises a 16S rDNA sequence that is at least 99% identical to SEQ ID NO: 1. In still another embodiment, the *Agrobacterium* species comprises a 16S rDNA sequence that is identical to SEQ ID NO: 1. In still another embodiment, the *Agrobacterium* species is the isolate FA13.

In another embodiment, the endophytic bacterium is a species of *Pantoea*. In a particular embodiment, the *Pantoea* species is identified on the basis of its rDNA sequence, as outlined herein. In a particular embodiment, the *Pantoea* species comprises a 16S rDNA sequence that is at least 97% identical to SEQ ID NO: 2. In another embodiment, the *Pantoea* species comprises a 16S rDNA sequence that is at least 99% identical to SEQ ID NO: 2. In still another embodiment, the *Pantoea* species comprises a 16S rDNA sequence that is identical to SEQ ID NO: 2. In still another embodiment, the *Pantoea* species is the isolate FF34.

In another embodiment, the endophytic bacterium is a species of *Sphingobium*. In a particular embodiment, the *Sphingobium* species is identified on the basis of its rDNA sequence, as outlined herein. In a particular embodiment, the *Sphingobium* species comprises a 16S rDNA sequence that is at least 97% identical to SEQ ID NO: 3. In another embodiment, the *Sphingobium* species comprises a 16S rDNA sequence that is at least 99% identical to SEQ ID NO: 3. In still another embodiment, the *Sphingobium* species comprises a 16S rDNA sequence that is identical to SEQ ID NO: 3. In still another embodiment, the *Sphingobium* species is the isolate FC42.

In another embodiment, the endophytic bacterium is a species of *Pseudomonas*. In a particular embodiment, the *Pseudomonas* species is identified on the basis of its rDNA sequence, as outlined herein. In a particular embodiment, the *Pseudomonas* species comprises a 16S rDNA sequence that is at least 97% identical to SEQ ID NO: 4. In another embodiment, the *Pseudomonas* species comprises a 16S rDNA sequence that is at least 99% identical to SEQ ID NO: 4. In still another embodiment, the *Pseudomonas* species comprises a 16S rDNA sequence that is identical to SEQ ID NO: 4. In still another embodiment, the *Pseudomonas* species is the isolate FB12.

In another embodiment, the endophytic bacterium is a species of *Enterobacter*. In a particular embodiment, the *Enterobacter* species is identified on the basis of its rDNA sequence, as outlined herein. In a particular embodiment, the *Enterobacter* species comprises a 16S rDNA sequence that is at least 97% identical to SEQ ID NO: 5. In another embodiment, the *Enterobacter* species comprises a 16S rDNA sequence that is at least 99% identical to SEQ ID NO: 5. In still another embodiment, the *Enterobacter* species comprises a 16S rDNA sequence that is identical to SEQ ID NO: 5. In still another embodiment, the *Enterobacter* species is the isolate FD17.

In another embodiment, the endophytic bacterium is a species of *Micrococcus*. In a particular embodiment, the *Micrococcus* species is identified on the basis of its rDNA sequence, as outlined herein. In a particular embodiment, the *Micrococcus* species comprises a 16S rDNA sequence that is at least 97% identical to SEQ ID NO: 6. In another embodiment, the *Micrococcus* species comprises a 16S rDNA sequence that is at least 99% identical to SEQ ID NO: 6. In still another embodiment, the *Micrococcus* species comprises a 16S rDNA sequence that is identical to SEQ ID NO: 6. In still another embodiment, the *Micrococcus* species is the isolate S2.

In another embodiment, the endophytic bacterium is a species of *Bacillus*. In a particular embodiment, the *Bacillus* species is identified on the basis of its rDNA sequence, as outlined herein. In a particular embodiment, the *Bacillus* species comprises a 16S rDNA sequence that is at least 97% identical to SEQ ID NO: 7. In another embodiment, the *Bacillus* species comprises a 16S rDNA sequence that is at least 99% identical to SEQ ID NO: 7. In still another embodiment, the *Bacillus* species comprises a 16S rDNA sequence that is identical to SEQ ID NO: 7. In still another embodiment, the *Bacillus* species is the isolate S4.

In another embodiment, the endophytic bacterium is a species of *Pantoea*. In a particular embodiment, the *Pantoea* species is identified on the basis of its rDNA sequence, as outlined herein. In a particular embodiment, the *Pantoea* species comprises a 16S rDNA sequence that is at least 97% identical to SEQ ID NO: 8. In another embodiment, the *Pantoea* species comprises a 16S rDNA sequence that is at least 99% identical to SEQ ID NO: 8. In still another embodiment, the *Pantoea* species comprises a 16S rDNA sequence that is identical to SEQ ID NO: 8. In still another embodiment, the *Pantoea* species is the isolate S6.

In another embodiment, the endophytic bacterium is a species of *Acinetobacter*. In a particular embodiment, the *Acinetobacter* species is identified on the basis of its rDNA sequence, as outlined herein. In a particular embodiment, the *Acinetobacter* species comprises a 16S rDNA sequence that is at least 97% identical to SEQ ID NO: 9. In another embodiment, the *Acinetobacter* species comprises a 16S rDNA sequence that is at least 99% identical to SEQ ID NO: 9. In still another embodiment, the *Acinetobacter* species comprises a 16S rDNA sequence that is identical to SEQ ID NO: 9. In still another embodiment, the *Acinetobacter* species is the isolate S9.

In another embodiment, the endophytic bacterium is a species of *Paenibacillus*. In a particular embodiment, the *Paenibacillus* species is identified on the basis of its rDNA sequence, as outlined herein. In a particular embodiment, the *Paenibacillus* species comprises a 16S rDNA sequence that is at least 97% identical to SEQ ID NO: 10. In another embodiment, the *Paenibacillus* species comprises a 16S rDNA sequence that is at least 99% identical to SEQ ID NO: 10. In still another embodiment, the *Paenibacillus* species comprises a 16S rDNA sequence that is identical to SEQ ID NO: 10. In still another embodiment, the *Paenibacillus* species is the isolate S10.

In some cases, the endophytic microbe can be modified. For example, the endophytic microbe can be genetically modified by introduction of a transgene which stably integrates into the bacterial genome. In another embodiment, the endophytic microbe can be modified to harbor a plasmid or episome containing a transgene. In still another embodiment, the microbe can be modified by repeated passaging under selective conditions.

The microbe can be modified to exhibit altered characteristics. In one embodiment, the endophytic microbe is modified to exhibit increased compatibility with chemicals commonly used in agriculture. Agricultural plants are often treated with a vast array of agrichemicals, including fungicides, biocides (anti-bacterial agents), herbicides, insecticides, nematicides, rodenticides, fertilizers, and other agents. Many such agents can affect the ability of an endophytic bacterium to grow, divide, and/or otherwise confer beneficial traits to the plant.

In some cases, it can be important for the microbe to be compatible with agrichemicals, particularly those with fungicidal or antibacterial properties, in order to persist in the plant although, as mentioned earlier, there are many such fungicidal or antibacterial agents that do not penetrate the plant, at least at a concentration sufficient to interfere with the microbe. Therefore, where a systemic fungicide or antibacterial agent is used in the plant, compatibility of the microbe to be inoculated with such agents will be an important criterion.

In one embodiment, spontaneous isolates of microbes which are compatible with agrichemicals can be used to inoculate the plants according to the methods described herein. For example, fungal microbes which are compatible with agriculturally employed fungicides can be isolated by plating a culture of the microbes on a petri dish containing an effective concentration of the fungicide, and isolating colonies of the microbe that are compatible with the fungicide. In another embodiment, a microbe that is compatible with a fungicide is used for the methods described herein. In still another embodiment, a microbe that is compatible with an antibacterial compound is used for the methods described herein. Fungicide compatible microbes can also be isolated by selection on liquid medium. The culture of microbes can be plated on petri dishes without any forms of mutagenesis; alternatively, the microbes can be mutagenized using any means known in the art. For example, microbial cultures can be exposed to UV light, gamma-irradiation, or chemical mutagens such as ethylmethanesulfonate (EMS) prior to selection on fungicide containing media. Finally, where the mechanism of action of a particular fungicide is known, the target gene can be specifically mutated (either by gene deletion, gene replacement, site-directed mutagenesis, etc.) to generate a microbe that is resilient against that particular fungicide. It is noted that the above-described methods can be used to isolate fungi that are compatible with both fungistatic and fungicidal compounds.

It will also be appreciated by one skilled in the art that a plant may be exposed to multiple types of fungicides or antibacterial compounds, either simultaneously or in succession, for example at different stages of plant growth. Where the target plant is likely to be exposed to multiple fungicidal and/or antibacterial agents, a microbe that is compatible with many or all of these agrichemicals can be used to inoculate the plant. A microbe that is compatible with several fungicidal agents can be isolated, for example, by serial selection. A microbe that is compatible with the first fungicidal agent is isolated as described above (with or without prior mutagenesis). A culture of the resulting microbe can then be selected for the ability to grow on liquid or solid media containing the second antifungal compound (again, with or without prior mutagenesis). Colonies isolated from the second selection are then tested to confirm its compatibility to both antifungal compounds.

Likewise, bacterial microbes that are compatible to biocides (including herbicides such as glyphosate or antibacterial compounds, whether bacteriostatic or bactericidal) that are agriculturally employed can be isolated using methods similar to those described for isolating fungicide compatible microbes. In one embodiment, mutagenesis of the microbial population can be performed prior to selection with an antibacterial agent. In another embodiment, selection is performed on the microbial population without prior mutagenesis. In still another embodiment, serial selection is performed on a microbe: the microbe is first selected for compatibility to a first antibacterial agent. The isolated compatible microbe is then cultured and selected for compatibility to the second antibacterial agent. Any colony thus isolated is tested for compatibility to each, or both antibacterial agents to confirm compatibility with these two agents.

The selection process described above can be repeated to identify isolates of the microbe that are compatible with a multitude of antifungal or antibacterial agents.

Candidate isolates can be tested to ensure that the selection for agrichemical compatibility did not result in loss of a desired microbial bioactivity. Isolates of the microbe that are compatible with commonly employed fungicides can be selected as described above. The resulting compatible microbe can be compared with the parental microbe on plants in its ability to promote germination.

Plant-Endophyte Combinations

In another aspect, the present invention provides for combinations of endophytes and plants. In one embodiment, disclosed is a seed or seedling of an agricultural plant comprising an exogenous endophytic bacterial population that is disposed on an exterior surface of or within the seed or seedling in an amount effective to colonize the plant, and further comprising a formulation that comprises at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient. In another embodiment, the present invention discloses a seed or seedling of an agricultural plant comprising an endophytic bacterial population that is heterologously disposed on an exterior surface of or within the seed or seedling in an amount effective to colonize the plant, and further comprising a formulation that comprises at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient.

The endophytic bacterial population consists essentially of an endophytic bacterium described herein. In one embodiment, the endophytic bacterium comprises a 16S rRNA nucleic acid sequence that is at least 97% identical to a nucleic acid sequence selected from the group consisting of SEQ ID NOs: 1-10. In another embodiment, the endophytic bacterium comprises a 16S rRNA nucleic acid sequence that is at least 99% identical to a nucleic acid sequence selected from the group consisting of SEQ ID NOs: 1-10. In still another embodiment, the endophytic bacterium comprises a 16S rRNA nucleic acid sequence that is identical to a nucleic acid sequence selected from the group consisting of SEQ ID NOs: 1-10.

In one embodiment according to this aspect, disclosed is a seed of an agricultural plant comprising an exogenous endophytic bacterial population that is disposed on an exterior surface of or within the seed in an amount effective to colonize the plant. The bacterial population is considered exogenous to the seed if that particular seed does not inherently contain the bacterial population. Indeed, several of the endophytic microbes described herein have not been detected, for example, in any of the corn seeds sampled, as determined by highly sensitive methods.

In other cases, the present invention discloses a seed of an agricultural plant comprising an endophytic bacterial population that is heterologously disposed on an exterior surface of or within the seed in an amount effective to colonize the plant. For example, the endophytic bacterial population that is disposed on an exterior surface or within the seed can be an endophytic bacterium that may be associated with the mature plant, but is not found on the surface of or within the seed. Alternatively, the endophytic bacterial population can be found in the surface of, or within the seed, but at a much lower number than is disposed.

As shown in the Examples section below, the endophytic bacterial populations described herein are capable of colonizing the host plant. In certain cases, the endophytic bacterial population can be applied to the plant, for example the plant seed, or by foliar application, and successful colonization can be confirmed by detecting the presence of the bacterial population within the plant. For example, after applying the bacteria to the seeds, high titers of the bacteria can be detected in the roots and shoots of the plants that germinate from the seeds. In addition, significant quantities of the bacteria can be detected in the rhizosphere of the plants. Therefore, in one embodiment, the endophytic microbe population is disposed in an amount effective to colonize the plant. Colonization of the plant can be detected, for example, by detecting the presence of the endophytic microbe inside the plant. This can be accomplished by measuring the viability of the microbe after surface sterilization of the seed or the plant: endophytic colonization results in an internal localization of the microbe, rendering it resistant to conditions of surface sterilization. The presence and quantity of the microbe can also be established using other means known in the art, for example, immunofluorescence microscopy using microbe specific antibodies, or fluorescence in situ hybridization (see, for example, Amann et al. (2001) Current Opinion in Biotechnology 12:231-236, incorporated herein by reference in its entirety). Alternatively, specific nucleic acid probes recognizing conserved sequences from the endophytic bacterium can be employed to amplify a region, for example by quantitative PCR, and correlated to CFUs by means of a standard curve.

In another embodiment, the endophytic microbe is disposed in an amount effective to be detectable in the mature agricultural plant. In one embodiment, the endophytic microbe is disposed in an amount effective to be detectable in an amount of at least about 100 CFU, at least about 200 CFU, at least about 300 CFU, at least about 500 CFU, at least about 1,000 CFU, at least about 3,000 CFU, at least about 10,000 CFU, at least about 30,000 CFU, at least about 100,000 CFU or more in the mature agricultural plant.

In some cases, the endophytic microbe is capable of colonizing particular tissue types of the plant. In one embodiment, the endophytic microbe is disposed on the seed or seedling in an amount effective to be detectable within a target tissue of the mature agricultural plant selected from a fruit, a seed, a leaf, or a root, or portion thereof. For example, the endophytic microbe can be detected in an amount of at least about 100 CFU, at least about 200 CFU, at least about 300 CFU, at least about 500 CFU, at least about 1,000 CFU, at least about 3,000 CFU, at least about 10,000 CFU, at least about 30,000 CFU, at least about 100,000 CFU or more, in the target tissue of the mature agricultural plant.

In some cases, the microbes disposed on the seed or seedling can be detected in the rhizosphere. This may be due to successful colonization by the endophytic microbe, where certain quantities of the microbe is shed from the root, thereby colonizing the rhizosphere. In some cases, the rhizosphere-localized microbe can secrete compounds (such as siderophores or organic acids) which assist with nutrient acquisition by the plant. Therefore, in another embodiment, the endophytic microbe is disposed on the surface of the seed in an amount effective to detectably colonize the soil environment surrounding the mature agricultural plant when compared with a reference agricultural plant. For example, the microbe can be detected in an amount of at least 100 CFU/g DW, for example, at least 200 CFU/g DW, at least 500 CFU/g DW, at least 1,000 CFU/g DW, at least 3,000 CFU/g DW, at least 10,000 CFU/g DW, at least 30,000 CFU/g DW, at least 100,000 CFU/g DW, at least 300,000 CFU/g DW, or more, in the rhizosphere.

The endophytic bacterial populations described herein are also capable of providing many fitness benefits to the host plant. As shown in the Examples section, endophyte-inoculated plants display increased seed germination, increased vigor, increased biomass (e.g., increased root or shoot biomass), increased photochemical efficiency. Therefore, in one embodiment, the endophytic bacterial population is disposed on the surface or within a tissue of the seed or seedling in an amount effective to increase the biomass of the plant, or a part or tissue of the plant grown from the seed or seedling. The increased biomass is useful in the production of commodity products derived from the plant. Such commodity products include an animal feed, a fish fodder, a cereal product, a processed human-food product, a sugar or an alcohol. Such products may be a fermentation product or a fermentable product, one such exemplary product is a biofuel. The increase in biomass can occur in a part of the plant (e.g., the root tissue, shoots, leaves, etc.), or can be an increase in overall biomass. Increased biomass production, such an increase meaning at least about 10%, 20%, 30%, 40%, 50%, 60%, 70%, 80%, 90%, 100%, or greater than 100% when compared with a reference agricultural plant. Such increase in overall biomass can be under relatively stress-free conditions. In other cases, the increase in biomass can be in plants grown under any number of abiotic or biotic stresses, including drought stress, salt stress, heat stress, cold stress, low nutrient stress, nematode stress, insect herbivory stress, fungal pathogen stress, bacterial pathogen stress, and viral pathogen stress. In one particular embodiment, the endophytic bacterial population is disposed in an amount effective to increase root biomass by at least 10%, for example, at least 20%, at least 30%, at least 40%, at least 50%, at least 60%, at least 75%, at least 100%, or more, when compared with a reference agricultural plant.

In another embodiment, the endophytic bacterial population is disposed on the surface or within a tissue of the seed or seedling in an amount effective to increase the rate of seed germination when compared with a reference agricultural plant. For example, the increase in seed germination can be at least 10%, for example, at least 20%, at least 30%, at least 40%, at least 50%, at least 60%, at least 75%, at least 100%, or more, when compared with a reference agricultural plant.

In other cases, the endophytic microbe is disposed on the seed or seedling in an amount effective to increase the average biomass of the fruit or cob from the resulting plant by at least 10%, for example, at least 20%, at least 30%, at least 40%, at least 50%, at least 75%, at least 100% or more, when compared with a reference agricultural plant.

As highlighted in the Examples section, plants inoculated with the endophytic bacterial population also show an increase in overall plant height. Therefore, in one embodiment, the present invention provides for a seed comprising an endophytic bacterial population which is disposed on the surface or within a tissue of the seed or seedling in an amount effective to increase the height of the plant. For example, the endophytic bacterial population is disposed in an amount effective to result in an increase in height of the agricultural plant such that is at least 10% greater, for example, at least 20% greater, at least 30% greater, at least 40% greater, at least 50% greater, at least 60% greater, at least 70% greater, at least 80% greater, at least 90% greater, at least 100% greater, at least 125% greater, at least 150% greater or more, when compared with a reference agricultural plant, the plant. Such increase in height can be under relatively stress-free conditions. In other cases, the increase in height can be in plants grown under any number of abiotic or biotic stresses, including drought stress, salt stress, heat stress, cold stress, low nutrient stress, nematode stress, insect herbivory stress, fungal pathogen stress, bacterial pathogen stress, and viral pathogen stress.

The host plants inoculated with the endophytic bacterial population also show dramatic improvements in their ability to utilize water more efficiently. Water use efficiency is a parameter often correlated with drought tolerance. Water use efficiency (WUE) is a parameter often correlated with drought tolerance, and is the $CO_2$ assimilation rate per water transpired by the plant. An increase in biomass at low water availability may be due to relatively improved efficiency of growth or reduced water consumption. In selecting traits for improving crops, a decrease in water use, without a change in growth would have particular merit in an irrigated agricultural system where the water input costs were high. An increase in growth without a corresponding jump in water use would have applicability to all agricultural systems. In many agricultural systems where water supply is not limiting, an increase in growth, even if it came at the expense of an increase in water use also increases yield.

When soil water is depleted or if water is not available during periods of drought, crop yields are restricted. Plant water deficit develops if transpiration from leaves exceeds the supply of water from the roots. The available water supply is related to the amount of water held in the soil and the ability of the plant to reach that water with its root system. Transpiration of water from leaves is linked to the fixation of carbon dioxide by photosynthesis through the stomata. The two processes are positively correlated so that high carbon dioxide influx through photosynthesis is closely linked to water loss by transpiration. As water transpires from the leaf, leaf water potential is reduced and the stomata tend to close in a hydraulic process limiting the amount of photosynthesis. Since crop yield is dependent on the fixation of carbon dioxide in photosynthesis, water uptake and transpiration are contributing factors to crop yield. Plants which are able to use less water to fix the same amount of carbon dioxide or which are able to function normally at a lower water potential have the potential to conduct more photosynthesis and thereby to produce more biomass and economic yield in many agricultural systems. An increased water use efficiency of the plant relates in some cases to an increased fruit/kernel size or number.

Therefore, in one embodiment, the plants described herein exhibit an increased water use efficiency when compared with a reference agricultural plant grown under the same conditions. For example, the plants grown from the seeds comprising the endophytic bacterial population can have at least 5% higher WUE, for example, at least 10% higher, at least 20% higher, at least 30% higher, at least 40% higher, at least 50% higher, at least 60% higher, at least 70% higher, at least 80% higher, at least 90% higher, at least 100% higher WUE than a reference agricultural plant grown under the same conditions. Such an increase in WUE can occur under conditions without water deficit, or under conditions of water deficit, for example, when the soil water content is less than or equal to 60% of water saturated soil, for example, less than or equal to 50%, less than or equal to 40%, less than or equal to 30%, less than or equal to 20%, less than or equal to 10% of water saturated soil on a weight basis.

In a related embodiment, the plant comprising the endophytic bacterial endophyte can have at least 10% higher relative water content (RWC), for example, at least 20% higher, at least 30% higher, at least 40% higher, at least 50% higher, at least 60% higher, at least 70% higher, at least 80% higher, at least 90% higher, at least 100% higher RWC than a reference agricultural plant grown under the same conditions.

Many of the microbes described herein are capable of producing the plant hormone auxin indole acetic acid (IAA) when grown in culture. Auxin may play a key role in altering the physiology of the plant, including the extent of root growth. Therefore, in another embodiment, the endophytic bacterial population is disposed on the surface or within a tissue of the seed or seedling in an amount effective to detectably induce production of auxin in the agricultural plant. For example, the increase in auxin production can be at least 10%, for example, at least 20%, at least 30%, at least 40%, at least 50%, at least 60%, at least 75%, at least 100%, or more, when compared with a reference agricultural plant. In one embodiment, the increased auxin production can be detected in a tissue type selected from the group consisting of the root, shoot, leaves, and flowers.

In another embodiment, the endophytic bacterial population of the present invention can cause a detectable modulation in the amount of a metabolite in the plant or part of the plant. Such modulation can be detected, for example, by measuring the levels of a given metabolite and comparing with the levels of the metabolite in a reference agricultural plant grown under the same conditions.

Plants Useful for the Present Invention

The methods and compositions according to the present invention can be deployed for any seed plant species. Monocotyledonous as well as dicotyledonous plant species are particularly suitable. The methods and compositions are preferably used with plants that are important or interesting for agriculture, horticulture, for the production of biomass used in producing liquid fuel molecules and other chemicals, and/or forestry.

Thus, the invention has use over a broad range of plants, preferably higher plants pertaining to the classes of Angiospermae and Gymnospermae. Plants of the subclasses of the Dicotylodenae and the Monocotyledonae are particularly suitable. Dicotyledonous plants belong to the orders of the Aristochiales, Asterales, Batales, Campanulales, Capparales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Middles, Juglandales, Lamiales, Laurales, Lecythidales, Leitneriales, Magniolales, Malvales, Myricales, Myrtales, Nymphaeales, Papeverales, Piperales, Plantaginales, Plumb aginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Theales, Trochodendrales, Umbellales, Urticales, and Violates. Monocotyledonous plants belong to the orders of the Alismatales, Arales, Arecales, Bromeliales, Commelinales, Cyclanthales, Cyperales, Eriocaulales, Hydrocharitales, Juncales, Lilliales, Najadales, Orchidales, Pandanales, Poales, Restionales, Triuridales, Typhales, and Zingiberales. Plants belonging to the class of the Gymnospermae are Cycadales, Ginkgoales, Gnetales, and Pinales.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

The methods and compositions of the present invention are preferably used in plants that are important or interesting for agriculture, horticulture, biomass for the production of biofuel molecules and other chemicals, and/or forestry. Non-limiting examples include, for instance, *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp., *Sorghum* spp., *Miscanthus* spp., *Saccharum* spp., *Erianthus* spp., *Populus* spp., *Secale cereale* (rye), *Salix* spp. (willow), *Eucalyptus* spp. (eucalyptus), *Triticosecale* spp. (*triticum*—wheat X rye), Bamboo, *Carthamus tinctorius* (safflower), *Jatropha curcas* (Jatropha), *Ricinus communis* (castor), *Elaeis guineensis* (oil palm), *Phoenix dactylifera* (date palm), *Archontophoenix cunninghamiana* (king palm), *Syagrus romanzoffiana* (queen palm), *Linum usitatissimum* (flax), *Brassica juncea, Manihot esculenta* (cassava), *Lycopersicon esculentum* (tomato), *Lactuca saliva* (lettuce), *Musa paradisiaca* (banana), *Solanum tuberosum* (potato), *Brassica oleracea* (broccoli, cauliflower, brusselsprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale, Taxus baccata, Taxus brevifolia, Artemisia annua, Cannabis saliva, Camptotheca acuminate, Catharanthus roseus, Vinca rosea, Cinchona officinalis, Coichicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii, Tanacetum parthenium, Parthenium argentatum* (guayule), *Hevea* spp. (rubber), *Mentha spicata* (mint), *Mentha piperita* (mint), *Bixa orellana, Alstroemeria* spp., *Rosa* spp. (rose), *Dianthus caryophyllus* (carnation), *Petunia* spp. (*petunia*), *Poinsettia pulcherrima* (poinsettia), *Nicotiana tabacum* (tobacco), *Lupinus albus* (lupin), *Uniola paniculata* (oats), *Hordeum vulgare* (barley), and *Lolium* spp. (ryegrass).

The methods described herein can also be used with genetically modified plants, for example, to yield additional trait benefits to a plant. For example, a genetically modified plant which is, by means of the transgene, optimized with respect to a certain trait, can be further augmented with additional trait benefits conferred by the newly introduced microbe. Therefore, in one embodiment, a genetically modified plant is contacted with a microbe.

Formulations/Seed Coating Compositions

In some embodiments, the present invention contemplates seeds comprising a endophytic bacterial population, and further comprising a formulation. The formulation useful for these embodiments generally comprise at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient.

In some cases, the endophytic bacterial population is mixed with an agriculturally compatible carrier. The carrier can be a solid carrier or liquid carrier. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in a composition of the invention. Water-in-oil emulsions can also be used to formulate a composition that includes the endophytic bacterial population of the present invention (see, for example, U.S. Pat. No. 7,485,451, which is incorporated herein by reference in its entirety). Suitable formulations that may be prepared include wettable powders, granules, gels, agar strips or pellets, thickeners, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or plant growth medium. Other agricultural carriers that may be used include fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, or other biological materials such as seed, plant parts, sugar cane bagasse, hulls or stalks from grain processing, ground plant material or wood from building site refuse, sawdust or small fibers from recycling of paper, fabric, or wood. Other suitable formulations will be known to those skilled in the art.

In one embodiment, the formulation can comprise a tackifier or adherent. Such agents are useful for combining the bacterial population of the invention with carriers that can contain other compounds (e.g., control agents that are not biologic), to yield a coating composition. Such compositions help create coatings around the plant or seed to maintain contact between the microbe and other agents with the plant or plant part. In one embodiment, adherents are selected from the group consisting of: alginate, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers. Other examples of adherent compositions that can be used in the synthetic preparation include those described in EP 0818135, CA 1229497, WO 2013090628, EP 0192342, WO 2008103422 and CA 1041788, each of which is incorporated herein by reference in its entirety.

The formulation can also contain a surfactant. Non-limiting examples of surfactants include nitrogen-surfactant blends such as Prefer 28 (Cenex), Surf-N(US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision). In one embodiment, the surfactant is present at a concentration of between 0.01% v/v to 10% v/v. In another embodiment, the surfactant is present at a concentration of between 0.1% v/v to 1% v/v.

In certain cases, the formulation includes a microbial stabilizer. Such an agent can include a desiccant. As used herein, a "desiccant" can include any compound or mixture of compounds that can be classified as a desiccant regardless of whether the compound or compounds are used in such concentrations that they in fact have a desiccating effect on the liquid inoculant. Such desiccants are ideally compatible with the bacterial population used, and should promote the ability of the microbial population to survive application on the seeds and to survive desiccation. Examples of suitable desiccants include one or more of trehalose, sucrose, glycerol, and methylene glycol. Other suitable desiccants include, but are not limited to, non reducing sugars and sugar alcohols (e.g., mannitol or sorbitol). The amount of desiccant introduced into the formulation can range from about 5% to about 50% by weight/volume, for example, between about 10% to about 40%, between about 15% and about 35%, or between about 20% and about 30%.

In some cases, it is advantageous for the formulation to contain agents such as a fungicide, an antibacterial agent, an herbicide, a nematicide, an insecticide, a plant growth regulator, a rodenticide, and a nutrient. Such agents are ideally compatible with the agricultural seed or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

In the liquid form, for example, solutions or suspensions, the endophytic bacterial populations of the present invention can be mixed or suspended in aqueous solutions. Suitable liquid diluents or carriers include aqueous solutions, petroleum distillates, or other liquid carriers.

Solid compositions can be prepared by dispersing the endophytic bacterial populations of the invention in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

In one particular embodiment, the formulation is ideally suited for coating of the endophytic microbial population onto seeds. The endophytic bacterial populations described in the present invention are capable of conferring many fitness benefits to the host plants. The ability to confer such benefits by coating the bacterial populations on the surface of seeds has many potential advantages, particularly when used in a commercial (agricultural) scale.

The endophytic bacterial populations herein can be combined with one or more of the agents described above to yield a formulation suitable for combining with an agricultural seed or seedling. The bacterial population can be obtained from growth in culture, for example, using a synthetic growth medium. In addition, the microbe can be cultured on solid media, for example on petri dishes, scraped off and suspended into the preparation. Microbes at different growth phases can be used. For example, microbes at lag phase, early-log phase, mid-log phase, late-log phase, stationary phase, early death phase, or death phase can be used.

The formulations comprising the endophytic bacterial population of the present invention typically contains between about 0.1 to 95% by weight, for example, between about 1% and 90%, between about 3% and 75%, between about 5% and 60%, between about 10% and 50% in wet weight of the bacterial population of the present invention. It is preferred that the formulation contains at least about $10^3$ per ml of formulation, for example, at least about $10^4$, at least about $10^5$, at least about $10^6$, at least $10^7$ CFU, at least $10^8$ CFU per ml of formulation.

As described above, in certain embodiments, the present invention contemplates the use of endophytic bacteria that are heterologously disposed on the plant, for example, the seed. In certain cases, the agricultural plant may contain bacteria that are substantially similar to, or even genetically indistinguishable from, the bacteria that are being applied to the plant. It is noted that, in many cases, the bacteria that are being applied is substantially different from the bacteria already present in several significant ways. First, the bacteria that are being applied to the agricultural plant have been adapted to culture, or adapted to be able to grow on growth media in isolation from the plant. Second, in many cases, the bacteria that are being applied are derived from a clonal origin, rather than from a heterologous origin and, as such, can be distinguished from the bacteria that are already present in the agricultural plant by the clonal similarity. For example, where a microbe that has been inoculated by a plant is also present in the plant (for example, in a different tissue or portion of the plant), or where the introduced microbe is sufficiently similar to a microbe that is present in some of the plants (or portion of the plant, including seeds), it is still possible to distinguish between the inoculated microbe and the native microbe by distinguishing between the two microbe types on the basis of their epigenetic status (e.g., the bacteria that are applied, as well as their progeny, would be expected to have a much more uniform and similar pattern of cytosine methylation of its genome, with respect to the extent and/or location of methylation).

Population of Seeds

In another aspect, the invention provides for a substantially uniform population of seeds comprising a plurality of seeds comprising the endophytic bacterial population, as described herein above. Substantial uniformity can be determined in many ways. In some cases, at least 10%, for example, at least 20%, at least 30%, at least 40%, at least 50%, at least 60%, at least 70%, at least 75%, at least 80%, at least 90%, at least 95% or more of the seeds in the population, contains the endophytic bacterial population in an amount effective to colonize the plant disposed on the surface of the seeds. In other cases, at least 10%, for example, at least 20%, at least 30%, at least 40%, at least 50%, at least 60%, at least 70%, at least 75%, at least 80%, at least 90%, at least 95% or more of the seeds in the population, contains at least 100 CFU on its surface, for example, at least 200 CFU, at least 300 CFU, at least 1,000 CFU, at least 3,000 CFU, at least 10,000 CFU, at least 30,000 CFU, at least 100,000 CFU, at least 300,000 CFU, or at least 1,000,000 CFU per seed or more.

In a particular embodiment, the population of seeds is packaged in a bag or container suitable for commercial sale. Such a bag contains a unit weight or count of the seeds comprising the endophytic bacterial population as described herein, and further comprises a label. In one embodiment, the bag or container contains at least 1,000 seeds, for example, at least 5,000 seeds, at least 10,000 seeds, at least 20,000 seeds, at least 30,000 seeds, at least 50,000 seeds, at least 70,000 seeds, at least 80,000 seeds, at least 90,000 seeds or more. In another embodiment, the bag or container can comprise a discrete weight of seeds, for example, at least 1 lb, at least 2 lbs, at least 5 lbs, at least 10 lbs, at least 30 lbs, at least 50 lbs, at least 70 lbs or more. The bag or container comprises a label describing the seeds and/or said endophytic bacterial population. The label can contain additional information, for example, the information selected from the group consisting of: net weight, lot number, geographic origin of the seeds, test date, germination rate, inert matter content, and the amount of noxious weeds, if any. Suitable containers or packages include those traditionally used in plant seed commercialization. The invention also contemplates other containers with more sophisticated storage capabilities (e.g., with microbiologically tight wrappings or with gas- or water-proof containments).

In some cases, a sub-population of seeds comprising the endophytic bacterial population is further selected on the basis of increased uniformity, for example, on the basis of uniformity of microbial population. For example, individual seeds of pools collected from individual cobs, individual plants, individual plots (representing plants inoculated on the same day) or individual fields can be tested for uniformity of microbial density, and only those pools meeting specifications (e.g., at least 80% of tested seeds have minimum density, as determined by quantitative methods described elsewhere) are combined to provide the agricultural seed subpopulation.

The methods described herein can also comprise a validating step. The validating step can entail, for example, growing some seeds collected from the inoculated plants into mature agricultural plants, and testing those individual plants for uniformity. Such validating step can be performed on individual seeds collected from cobs, individual plants, individual plots (representing plants inoculated on the same day) or individual fields, and tested as described above to identify pools meeting the required specifications.

Population of Plants/Agricultural Fields

A major focus of crop improvement efforts has been to select varieties with traits that give, in addition to the highest return, the greatest homogeneity and uniformity. While inbreeding can yield plants with substantial genetic identity, heterogeneity with respect to plant height, flowering time, and time to seed, remain impediments to obtaining a homogeneous field of plants. The inevitable plant-to-plant variability are caused by a multitude of factors, including uneven environmental conditions and management practices. Another possible source of variability can, in some cases, be due to the heterogeneity of the microbial population inhabit the plants. By providing endophytic bacterial populations onto seeds and seedlings, the resulting plants generated by germinating the seeds and seedlings have a more consistent microbial composition, and thus are expected to yield a more uniform population of plants.

Therefore, in another aspect, the invention provides a substantially uniform population of plants. The population comprises at least 100 plants, for example, at least 300 plants, at least 1,000 plants, at least 3,000 plants, at least 10,000 plants, at least 30,000 plants, at least 100,000 plants or more. The plants are grown from the seeds comprising the endophytic bacterial population as described herein. The increased uniformity of the plants can be measured in a number of different ways.

In one embodiment, there is an increased uniformity with respect to the microbes within the plant population. For example, in one embodiment, a substantial portion of the population of plants, for example at least 10%, at least 20%, at least 30%, at least 40%, at least 50%, at least 60%, at least 70%, at least 75%, at least 80%, at least 90%, at least 95% or more of the seeds or plants in a population, contains a threshold number of the endophytic bacterial population. The threshold number can be at least 100 CFU, for example at least 300 CFU, at least 1,000 CFU, at least 3,000 CFU, at least 10,000 CFU, at least 30,000 CFU, at least 100,000 CFU or more, in the plant or a part of the plant. Alternatively, in a substantial portion of the population of plants, for example, in at least 1%, at least 10%, at least 20%, at least 30%, at least 40%, at least 50%, at least 60%, at least 70%, at least 75%, at least 80%, at least 90%, at least 95% or more of the plants in the population, the endophytic bacterial population that is provided to the seed or seedling represents at least 10%, least 20%, at least 30%, at least 40%, at least 50%, at least 60%, at least 70%, at least 80%, at least 90%, at least 95%, at least 99%, or 100% of the total microbe population in the plant/seed.

In another embodiment, there is an increased uniformity with respect to a physiological parameter of the plants within the population. In some cases, there can be an increased uniformity in the height of the plants when compared with a population of reference agricultural plants grown under the same conditions. For example, there can be a reduction in the standard deviation in the height of the plants in the population of at least 5%, for example, at least 10%, at least 15%, at least 20%, at least 30%, at least 40%, at least 50%, at least 60% or more, when compared with a population of reference agricultural plants grown under the same conditions. In other cases, there can be a reduction in the standard deviation in the flowering time of the plants in the population of at least 5%, for example, at least 10%, at least 15%, at least 20%, at least 30%, at least 40%, at least 50%, at least 60% or more, when compared with a population of reference agricultural plants grown under the same conditions.

Commodity Plant Product

The present invention provides a commodity plant product, as well as methods for producing a commodity plant product, that is derived from a plant of the present invention. As used herein, a "commodity plant product" refers to any composition or product that is comprised of material derived from a plant, seed, plant cell, or plant part of the present invention. Commodity plant products may be sold to consumers and can be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, flakes, bran, fiber, paper, tea, coffee, silage, crushed or whole grain, and any other food for human or animal consumption; and biomasses and fuel products; and raw material in industry. Industrial uses of oils derived from the agricultural plants described herein include ingredients for paints, plastics, fibers, detergents, cosmetics, lubricants, and biodiesel fuel. Soybean oil may be split, inter-esterified, sulfurized, epoxidized, polymerized, ethoxylated, or cleaved. Designing and producing soybean oil derivatives with improved functionality and improved oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils to produce the desired type of oil or fat. Commodity plant products also include industrial compounds, such as a wide variety of resins used in the formulation of adhesives, films, plastics, paints, coatings and foams.

In some cases, commodity plant products derived from the plants, or using the methods of the present invention can be identified readily. In some cases, for example, the presence of viable endophytic microbes can be detected using the methods described herein elsewhere. In other cases, particularly where there are no viable endophytic microbes, the commodity plant product may still contain at least a detectable amount of the specific and unique DNA corresponding to the microbes described herein. Any standard method of detection for polynucleotide molecules may be used, including methods of detection disclosed herein.

Throughout the specification, the word "comprise," or variations such as "comprises" or "comprising," will be understood to imply the inclusion of a stated integer or group of integers but not the exclusion of any other integer or group of integers.

Although the present invention has been described in detail with reference to examples below, it is understood that various modifications can be made without departing from the spirit of the invention. For instance, while the particular examples below may illustrate the methods and embodiments described herein using a specific plant, the principles in these examples may be applied to any agricultural crop. Therefore, it will be appreciated that the scope of this invention is encompassed by the embodiments of the inventions recited herein and the specification rather than the specific examples that are exemplified below. All cited patents and publications referred to in this application are herein incorporated by reference in their entirety.

EXAMPLES

Example 1

Phenotypic and Physiological Characterization of Microbes

Bacterial strains from overnight cultures in tryptic soy broth were streaked on tryptic soy agar (TSA) plates and incubated at 30° C. After 24 h, the color and shape of colonies were noted. Cell motility and colony shape were observed under light microscope (Nikon, Japan). The pH limits for bacterial growth was determined by adjusting the pH of the growth media to values between 5 and 12 in triplicates. Bacterial growth on different salt concentrations was tested in TSA medium containing 1-6% NaCl. Furthermore, the ability of the microbes to grow in methanol/ethanol as sole carbon source was analyzed by replacing the glucose with either methanol or ethanol.

Aggregate formation of bacterial strains can positively affect their dispersal and survival in the plant environment and adsorption to plant roots. The extent of aggregation formation was measured in six replicates following the method of Madi and Henis (1989) Plant Soil 115:89-98 (incorporated herein by reference) with some modifications. Aliquots of liquid culture containing aggregates were transferred to glass tubes and allowed to stand for 30 min. Aggregates settled down to the bottom of each tubes, and the suspension was mostly composed free of cells. The turbidity of each suspension was measured at 540 nm (ODs) with a microplate reader (Synergy 5; BioTek Instrument Inc., Winooski, USA). Cultures were then dispersed with a tissue homogenizer for 1 min and the total turbidity (OD) was measured. The percentage of aggregation was estimated as follows:

$$\% \text{ aggregation} = (ODt - ODs) \times 100 / ODt$$

Motility assays (swimming, swarming and twitching) were performed following the methods of Rashid and Kornberg (2000). Swim plates (LB media contained 0.3% agarose) were inoculated in triplicates with bacteria from an overnight culture on TSA agar plates grown at 30° C. with a sterile toothpick. For swarming, plates (NB media contained 0.5% agar and glucose) were inoculated with a sterile toothpick. Twitch plates (LB broth containing 1% Difco granular agar) were stab inoculated with a sharp toothpick to the bottom of petri dish from an overnight grown culture in TSA agar plates.

Biofilm formation was analyzed using overnight grown bacterial culture in 96 well microtiter plates by staining with 1% crystal violet (CV) for 45 min. To quantify the amount of biofilm, CV was destained with 200 µl of 100% ethanol. The absorbance of 150 µl of the destained CV, which was transferred into a new microtiter plate was measured at 595 nm (modified from Djordjevic et al. 2002, Appl Environ Microbiol 68:2950-2958, incorporated herein by reference).

The phenotypic characteristics of the strains are shown below in Table 1:

| Characteristics | Agrobacterium sp. (FA13) | Pantoea sp. (FF34) | Sphinogobium sp. (FC42) | Pseudomonas sp. (FB12) | Enterobacter sp. (FD17) | Micrococus sp. S2 | Bacillus sp. S4 | Pantoea sp. S6 | Acinetobacter sp. S9 | Paenibacillus sp. S10 |
|---|---|---|---|---|---|---|---|---|---|---|
| \multicolumn{11}{c}{Phenotypic and physiological characterization} ||||||||||
| Colony color | Gray | Yellow | Yellow | Gray | Creamy white | Creamy | Off-white | Yellow | White | Creamy white |
| Colony morphology | Round | Round | Round | Round | Round | Round | Round | Round | Round | Round |
| Gram reaction | n.d. | n.d. | n.d. | n.d. | n.d. | positive | positive | negative | negative | negative |
| Bacterial growth conditions* Temperature ||||||||||| 
| 4° C. | n.d. | n.d. | n.d. | n.d. | n.d. | − | + | + | + | + |
| 42° C. | n.d. | n.d. | n.d. | n.d. | n.d. | − | − | − | − | − |
| NaCl ||||||||||| 
| 2% | + | + | + | + | + | + | + | + | + | + |
| 6% | − | + | − | − | + | + | + | + | − | + |
| pH ||||||||||| 
| 5 | + | + | + | + | + | + | + | + | + | + |
| 12 | + | − | − | + | + | + | − | + | − | + |
| Motility/chemotaxis‡ ||||||||||| 
| Swimming | + | + | − | ++ | +++ | − | − | + | − | ++ |
| Swarming | − | − | − | − | + | − | − | ++ | − | + |
| Twitching | + | + | − | + | + | − | + | + | − | + |
| Biofilm formation ||||||||||| 
| OD (600 nm) | 0.92 ± 0.04 | 0.59 ± 0.02 | 0.95 ± 0.08 | 0.57 ± 0.08 | 0.95 ± 0.04 | 0.92 ± 0.04 | 0.59 ± 0.02 | 0.95 ± 0.08 | 0.57 ± 0.08 | 0.95 ± 0.04 |
| Biofilm (595 nm) | 0.23 ± 0.02 | 0.22 ± 0.03 | 0.08 ± 0.01 | 0.08 ± 0.04 | 0.83 ± 0.06 | 0.23± 0.02 | 0.22 ± 0.03 | 0.08 ± 0.01 | 0.08 ± 0.04 | 0.83 ± 0.06 |
| Aggregate stability (%) | 35.91 ± 2.57 | 26.07 ± 0.88 | 32.61 ± 2.13 | 36.38 ± 1.48 | 40.22 ± 1.99 | 35.91 ± 2.57 | 26.07 ± 0.88 | 32.61 ± 2.13 | 36.38 ± 1.48 | 40.22 ± 1.99 |

Biochemical Characterization

Biochemical tests such as oxidase, catalase, gelatin hydrolysis and casein hydrolysis of the selected strains were performed. Oxidase and catalase activities were tested with 1% (w/v) tetramethyl-p-phenylene diamine and 3% (v/v) hydrogen peroxide solution, respectively. Gelatin and casein hydrolysis was performed by streaking bacterial strains onto a TSA plates from the stock culture. After incubation, trichloroacetic acid (TCA) was applied to the plates and made observation immediately for a period of at least 4 min (Medina and Baresi 2007, J Microbiol Methods 69:391-393, incorporated herein by reference). A summary of the biochemical characteristics of the strains is shown below in Table 2:

TABLE 2

Biochemical Characterization of Endophytic Bacteria
Biochemical characterization*

| | Agrobacterium sp. (FA13) | Pantoea sp. (FF34) | Sphinogobium sp. (FC42) | Pseudomonas sp. (FB12) | Enterobacter sp. (FD17) | Micrococus sp. S2 | Bacillus sp. S4 | Pantoea sp. S6 | Acinetobacter sp. S9 | Paenibacillus sp. S10 |
|---|---|---|---|---|---|---|---|---|---|---|
| Catalase | + | + | + | + | + | + | + | + | + | + |
| Oxidase | − | − | − | + | − | − | + | − | − | + |
| Casein | − | − | − | + | − | + | + | − | − | − |
| Gelatin | − | + | − | + | + | + | − | + | − | − |
| Methanol | + | − | − | + | − | + | − | − | + | + |
| Ethanol | + | − | − | + | − | + | − | − | + | + |

Quantification of Auxin Production

Auxin production by bacterial isolates both in the presence and absence of L-tryptophan (L-TRP) was determined colorimetrically and expressed as IAA equivalent (Sarwar et al. 1992, Plant Soil 147:207-215, incorporated herein by reference). Two days old bacterial cells grown (28° C. at 180 rpm) in tryptic soy broth supplemented with 1% L-TRP solution were harvested by centrifugation (10,000 g for 10 min). Three mL of the supernatants were mixed with 2 mL Salkowski's reagent (12 g $L^{-1}$ $FeCl_3$ in 429 ml $L^{-1}$ $H_2SO_4$). The mixture was incubated at room temperature for 30 min for colour development and absorbance at 535 nm was measured using spectrophotometer. Auxin concentration produced by bacterial isolates was determined using standard curves for IAA prepared from serial dilutions of 10-100 μg $mL^{-1}$.

TABLE 3

Production of Indole Acetic Acid by Endophytic Bacteria

| Charac-<br>teristics | *Agrobacterium*<br>sp. (FA13) | *Pantoea*<br>sp. (FF34) | *Sphinogobium*<br>sp. (FC42) | *Pseudomonas*<br>sp. (FB12) | *Enterobacter*<br>sp. (FD17) |
|---|---|---|---|---|---|
| without<br>L-TRP | 1.74 ±<br>0.18 | 10.33 ±<br>0.35 | 4.89 ±<br>0.78 | 1.63 ±<br>0.65 | 7.54 ±<br>1.02 |
| with<br>L-TRP | 16.13 ±<br>1.05 | 95.34 ±<br>2.14 | 38.41 ±<br>1.78 | 7.26 ±<br>1.05 | 12.30 ±<br>0.98 |

As shown in Table 3 above, strains FA13, FF34, FC42, FB12 and FD17 were all shown to produce auxin (ranging from 1.63 to 10.33 μg $ml^{-1}$ in the absence of L-tryptophan), and the level of auxin production was greatly enhanced by the presence of L-tryptophan in the growth medium (at least 7.26 μg $ml^{-1}$).

Assays for Phosphorus Solubilization and Siderophore Production

Bacterial strains were evaluated for their ability to solubilize phosphates (organic/inorganic P). Aliquots (10 μL) of overnight bacterial growth culture in tryptic soy broth were spot inoculated onto NBRI—PBP (Mehta and Nautiyal 2001) and calcium/sodium phytate agar medium (Rosado et al. 1998). Solubilization of organic/inorganic phosphates was detected by the formation of a clear zone around the bacterial growth spot. Phosphate solubilization activity was also determined by development of clear zone around bacterial growth on Pikovskaya agar medium (Pikovskaya 1948, Mikrobiologiya 17:362-370, incorporated herein by reference). Bacterial isolates were assayed for siderophores production on the Chrome azurol S (CAS) agar medium described by Schwyn and Neilands (1987), Curr Microbiol 43:57-58 (incorporated herein by reference) as positive for siderophore production.

Assays for Exopolysaccharide, $NH_3$ and HCN Production

For exopolysaccharide (EPS) activity (qualitative), strains were grown on Weaver mineral media enriched with glucose and production of EPS was assessed visually (modified from Weaver et al. 1975, Arch Microbiol 105:207-216, incorporated herein by reference). The EPS production was monitored as floc formation (fluffy material) on the plates after 48 h of incubation at 28±2° C. Strains were tested for the production of ammonia ($NH_3$) in peptone water as described by Cappuccino and Sherman (1992), Biochemical activities of microorganisms. In: Microbiology, A Laboratory Manual. The Benjamin/Cummings Publishing Co. California, USA, pp 125-178, incorporated herein by reference. The bacterial isolates were screened for the production of hydrogen cyanide (HCN) by inoculating King's B agar plates amended with 4.4 g $L^{-1}$ glycine (Lorck 1948, Physiol Plant 1:142-146, incorporated herein by reference). Filter paper (Whatman no. 1) saturated with picrate solution (2% $Na_2CO_3$ in 0.5% picric acid) was placed in the lid of a petri plate inoculated with bacterial isolates. The plates were incubated at 28±2° C. for 5 days. HCN production was assessed by the colour change of yellow filter paper to reddish brown.

Assays for Poly-Hydroxybutyrate (PHB) and n-Acyl-Homoserine Lactone (AHL) Production The bacterial isolates were tested for PHB production (qualitative) following the viable colony staining methods using Nile red and Sudan black B (Juan et al. 1998 Appl Environ Microbiol 64:4600-4602; Spiekermann et al. 1999, Arch Microbiol 171:73-80, each of which is incorporated by reference). The LB plates with overnight bacterial growth were flooded with 0.02% Sudan black B for 30 min and then washed with ethanol (96%) to remove excess strains from the colonies. The dark blue coloured colonies were taken as positive for PHB production. Similarly, LB plates amended with Nile red (0.5 μL $mL^{-1}$) were exposed to UV light (312 nm) after appropriate bacterial growth to detect PHB production. Colonies of PHA-accumulating strains showed fluoresce under ultraviolet light. The bacterial strains were tested for AHL production following the method modified from Cha et al. (1998), Mol Plant-Microbe Interact 11:1119-1129 (incorporated herein by reference). The LB plates containing 40 μg $ml^{-1}$ X-Gal were plated with reporter strains (*A. tumefaciens* NTL4.pZLR4). The LB plates were spot inoculated with 10 μL of bacterial culture and incubated at 28±2° C. for 24 h. Production of AHL activity is indicated by a diffuse blue zone surrounding the test spot of culture. *Agrobacterium tumefaciens* NTL1 (pTiC58ΔaccR) was used as positive control and plate without reporter strain was considered as negative control.

TABLE 4

Various Biochemical Properties of Endophytic Bacteria

| Characteristics[†] | Agrobacterium sp. (FA13) | Pantoea sp. (FF34) | Sphinogobium sp. (FC42) | Pseudomonas sp. (FB12) | Enterobacter sp. (FD17) | Micrococus sp. S2 | Bacillus sp. S4 | Pantoea sp. S6 | Acinetobacter sp. S9 | Paenibacillus sp. S10 |
|---|---|---|---|---|---|---|---|---|---|---|
| P-solubilization (inorganic/organic P) | | | | | | | | | | |
| $Ca_3(PO_4)_2$ | − | ++ | − | + | +++ | − | − | + | − | + |
| $CaHPO_4$ | − | ++ | − | + | +++ | − | − | + | − | + |
| Ca-phytate | − | ++ | − | ++ | +++ | − | − | + | − | + |
| Na-phytate | − | ++ | − | ++ | +++ | − | − | + | − | + |
| Exopolysaccharide | ++ | − | + | − | + | − | − | − | − | + |
| $N_2$-fixation | + | + | − | − | + | − | − | + | − | − |
| HCN production | − | − | − | + | − | − | − | − | − | − |
| $NH_3$ production | + | + | + | + | + | + | + | + | + | + |
| Siderophore production | +++ | + | + | ++ | +++ | n.d. | − | n.d. | − | + |
| AHL | − | − | − | + | − | − | − | + | − | + |
| PHB | − | + | − | + | + | + | − | + | − | − |

As shown above, the bacteria described herein exhibit varying degrees of phosphate utilization. For example, strains FF34, FB12, FD17, S6, and S10 were capable of hydrolyzing $Ca_3(PO_4)_2$, $CaHPO_4$, Ca-phytate and Na-phytate. These strains, therefore, may be effective for increasing phosphate availability for host plants under conditions of limiting concentrations of soluble phosphate in the soil.

Siderophores are small, high-affinity iron chelating compounds secreted by microorganisms such as bacteria, fungi and grasses. siderophores. They bind to the available form of iron $Fe^{3+}$ in the rhizosphere, thus making it unavailable to the phytopathogens and protecting the plant health (Ahmad et al. 2008, Microbiol Res 163:173-181, incorporated herein by reference). Siderophores are known for mobilizing Fe and making it available to the plant. Several of the strains, including FA13, FF34, FC42, FB12, FD17 and S10 were found to produce significant levels of siderophore when tested in agar medium containing Chrom azurol S (CAS). Therefore, in one embodiment, the strains described above are effective in increasing iron availability to the host plant.

The ability of bacterial strains to utilize or metabolize different nitrogen sources was evaluated. Interestingly, four of the strains tested (FA13, FF34, FD17, and S6) were capable of growing in nitrogen-free medium, demonstrating their ability to fix nitrogen. Therefore, in one embodiment, these strains can be provided in an amount effective to increase nitrogen utilization in a host plant.

Bacterial survival and colonization in the plant environment are necessary for plant growth and yield. Recently, Zúñiga and colleagues (2013), Mol Plant-Microbe Interact 26:546-553 (incorporated herein by reference) described that the cell-to-cell communication (QS) system mediated by AHL is implicated in rhizosphere competence and colonization of Arabidopsis thaliana by B. phytofirmans PsJN. Motility, aggregate stability, and biofilm formation are important traits for root surface colonization (Danhorn and Fuqua 2007, Annu Rev Microbiol 61:401-422, incorporated herein by reference). Three strains (FB12, S6 and S10) were found to produce AHL. It should be noted, however, that the bacteria described here may have other communication systems. Aggregation and biofilm formation were common traits in all tested strains. In the case of motility, six strains (FA13, FF34, FB12, FD17, S6 and S10) were positive for swimming, while FD17, S6 and S10 also showed swarming. Therefore, in one embodiment, the seeds are provided with an amount of these strains in an amount effective to produce detectable levels of AHL. In another embodiment, seeds of an agricultural plant are provided with an amount of the bacterial endophyte population effective to form biofilms.

Bacteria were tested for production of exopolysaccharide (EPS) and poly-hydroxybutyrate (PHB). Bacterial EPS and PHB have been shown to provide protection from such environmental insults as desiccation, predation, and the effects of antibiotics (Gasser et al. 2009, FEMS Microbiol Ecol 70:142-150; Staudt et al. 2012, Arch Microbiol 194:197-206, each of which is incorporated by reference). They can also contribute to bacterial aggregation, surface attachment, and plant-microbe symbiosis (Laus et al. 2005, Mol Plant-Microbe Interact 18:533-538, incorporated herein by reference). Five strains (FF34, FB12, FD17, S2 and S6) showed PHB production, while FA13, FC42, FD17 and S10 were found to produce EPS. Therefore, in another embodiment, seeds of an agricultural plant are provided with an amount of the bacterial endophyte population effective to improve desiccation tolerance in the host plant.

Volatile compounds such as ammonia and HCN produced by a number of rhizobacteria were reported to play an important role in biocontrol (Brimecombe et al. 2001, In: Pinton R, Varanini Z, Nannipieri P (Eds.) The Rhizosphere, Marcel Dekker, New York, pp 95-140, incorporated herein by reference). Production of ammonia was commonly detected in all selected isolates. In contrast, only Pseudomonas sp. strain FB12 was able to produce HCN. Among the strains tested, only FB12 was able to produce HCN.

Enzyme Hydrolyzing Activities

Bacterial hydrolyzing activities due to amylase, cellulase, chitinase, hemolytic, lipase, pectinase, protease and xylanase were screened on diagnostic plates after incubation at 28° C. Amylase activity was determined on agar plates following the protocol Männistö and Häggblom (2006), Syst Appl Microbiol 29:229-243, incorporated herein by reference. Formation of opaque halo around colonies was used as an indication of lipase activity. Cellulase and xylanase activities were assayed on plates containing (per liter) 5 g of carboxymethyl cellulose or birch wood xylan, 1 g of peptone and 1 g of yeast extract. After 10 days of incubation, the plates were flooded with gram's iodine staining and washing with 1M NaCl to visualize the halo zone around the bacterial growth (modified from Teather and Wood 1982, Appl Environ Microbiol 43:777-780, incorporated herein by reference). Chitinase activity of the isolates was determined as zones of clearing around colonies following the method of Chemin et al. (1998) J Bacteriol 180:4435-4441 (incorporated herein by reference). Hemolytic activity was determined by streaking bacterial isolates onto Cloumbia 5% sheep blood agar plates. Protease activity was determined using 1% skimmed milk agar plates, while lipase activity was determined on peptone agar medium. Formation of halo zone around colonies was used as indication of activity (Smibert and Krieg 1994, In: Gerhardt P, Murray R, Wood W, Krieg N (Eds) Methods for General and Molecular Bacteriology, ASM Press, Washington, D.C., pp 615-640, incorporated herein by reference). Pectinase activity was determined on nutrient agar supplemented with 5 g $L^{-1}$ pectin. After 1 week of incubation, plates were flooded with 2% hexadecyl trimethyl ammonium bromide solution for 30 min. The plates were washed with 1M NaCl to visualize the halo zone around the bacterial growth (Mateos et al. 1992, Appl Environ Microbiol 58:1816-1822, incorporated herein by reference).

positive for cellulase and/or xylanase except strains FF34 and S9. Chitinase was produced by FB12, FD17 and S4 strains, while all strains tested except for FC42 showed hemolytic activity.

Antagonistic Activities Against Plant Pathogenic Bacteria, Fungi and Oomycetes

The antagonistic activities of bacterial isolates were screened against plant pathogenic bacteria (*Agrobacterium tumefaciens, Pseudomonas syringae, Streptococcus pneumoniae*), fungi (*Fusarium caulimons, Fusarium graminarium, Fusarium oxysporum, Fusarium solani, Rhizoctonia solani, Thielaviopsis basicola*) and oomycetes (*Phytophthora infestans, Phytophthora citricola, Phytophthora cominarum*). For antibacterial assays, the bacterial isolates and pathogen were cultivated in tryptic soy broth at 30° C. for 24 h. The bacterial isolates were spot-inoculated (10 μL aliquots) on TSA plates pre-seeded with 100 μL tested pathogen. The plates were incubated at 28° C. for 48 h and clear zones of inhibition were recorded. Antagonistic activity of the bacterial isolates against fungi and oomycetes was tasted by the dual culture technique on potato dextrose agar (PDA) and yeast malt agar (YMA) media (Dennis and Webster 1971, Trans Brit Mycol Soc 57:25-39, incorporated herein by reference). A small disk (5 mm) of target fungus/oomycetes was placed in the center of petri dishes of both media. Aliquots of

TABLE 5

Enzyme Activities from Endophytic Bacteria

| Characteristics | *Agrobacterium* sp. (FA13) | *Pantoea* sp. (FF34) | *Sphinogobium* sp. (FC42) | *Pseudomonas* sp. (FB12) | *Enterobacter* sp. (FD17) | *Micrococus* sp. S2 | *Bacillus* sp. S4 | *Pantoea* sp. S6 | *Acinetobacter* sp. S9 | *Paenibacillus* sp. S10 |
|---|---|---|---|---|---|---|---|---|---|---|
| Enzyme hydrolyzing activity‡ | | | | | | | | | | |
| Amylase | − | − | − | − | − | − | − | − | − | + |
| Cellulase | + | − | + | + | ++ | + | + | − | − | + |
| Chitinase | − | − | − | + | + | − | + | − | − | − |
| Hemolytic | + | + | − | + | + | n.d. | n.d. | n.d. | n.d. | n.d. |
| Lipase | ++ | + | + | +++ | ++ | − | + | + | + | + |
| Pectinase | − | + | − | + | + | − | − | + | − | + |
| Phosphatase | − | ++ | − | ++ | +++ | − | − | + | − | + |
| Protease | − | − | − | − | − | + | + | − | − | − |
| Xylanase | + | − | +++ | + | ++ | + | + | + | − | + |

All strains showed lipase activity, while only S10 produced amylase activity. S2 and S4 produced significant protease activity. Pectinase and phosphatase activity was observed with strains FF34, FB12, FD17, S6 and S10. All strains were 10 μL of overnight bacterial cultures grown in tryptic soy broth were spotted 2 cm away from the center. Plates were incubated for 14 days at 24° C. and zones of inhibition were scored.

TABLE 6

Antimicrobial Activity by Endophytic Bacteria

| Characteristics | *Agrobacterium* sp. (FA13) | *Pantoea* sp. (FF34) | *Sphinogobium* sp. (FC42) | *Pseudomonas* sp. (FB12) | *Enterobacter* sp. (FD17) | *Micrococus* sp. S2 | *Bacillus* sp. S4 | *Pantoea* sp. S6 | *Acinetobacter* sp. S9 | *Paenibacillus* sp. S10 |
|---|---|---|---|---|---|---|---|---|---|---|
| Anti-bacterial activity | | | | | | | | | | |
| *A. tumefaciens* | − | − | − | ++ | + | − | + | − | − | + |
| *E. coli* | n.d. | n.d. | n.d. | n.d. | n.d. | + | + | − | − | + |
| *P. syringae* | − | − | − | +++ | + | − | + | − | − | + |
| *S. aureus* | − | − | − | + | − | + | + | + | + | + |
| Anti-fungal activity | | | | | | | | | | |
| *F. caulimons* | ++ | + | + | ++ | +++ | − | + | + | − | + |
| *F. graminarium* | + | + | + | + | ++ | − | − | + | + | + |
| *F. oxysporum* | + | ++ | + | ++ | ++ | + | + | + | − | − |
| *F. solani* | ++ | + | ++ | ++ | +++ | − | + | − | − | + |

TABLE 6-continued

Antimicrobial Activity by Endophytic Bacteria

| Charac-teristics | Agrobacterium sp. (FA13) | Pantoea sp. (FF34) | Sphinogobium sp. (FC42) | Pseudomonas sp. (FB12) | Enterobacter sp. (FD17) | Micrococus sp. S2 | Bacillus sp. S4 | Pantoea sp. S6 | Acineto-bacter sp. S9 | Paeni-bacillus sp. S10 |
|---|---|---|---|---|---|---|---|---|---|---|
| R. solani | + | + | + | ++ | ++ | + | + | + | + | + |
| T. basicola | + | + | + | ++ | + | − | + | + | − | + |
| Anti-oomycete activity | | | | | | | | | | |
| P. infestans | + | + | + | ++ | ++ | − | − | + | − | − |
| P. citricola | + | + | + | ++ | +++ | − | − | + | + | + |
| P. cominarum | + | + | + | ++ | ++ | − | + | + | + | + |

Effect of Endophytic Strains on Maize Germination

Inoculants of the selected strains were prepared in 50 mL tryptic soy broth in 100 mL Erlenmeyer flasks and incubated at 28±2° C. for 48 h in the orbital shaking incubator (VWR International, GmbH) at 180 r min$^{-1}$. The optical density of the broth was adjusted to 0.5 measured at 600 nm using spectrophotometer (Gene Quant Pro, Gemini BV, The Netherlands) to obtain a uniform population of bacteria ($10^8$-$10^9$ colony-forming units (CFU) mL$^{-1}$) in the broth at the time of inoculation. More scientifically, harvested bacterial cells could be resuspended in the phosphate buffered saline. The inoculum density adjusts using a spectrophotometer to achieve population density (Pillay and Nowak 1997, Can J Microbiol 43:354-361, incorporated herein by reference).

Maize seeds were surface-sterilized with 70% ethanol (3 min), treated with 5% NaOHCl for 5 min, and followed by washing 3 times with sterile distilled water (1 min each time). The efficacy of surface sterilization was checked by plating seed, and aliquots of the final rinse onto LB plates. Samples were considered to be successfully sterilized when no colonies were observed on the LB plates after inoculation for 3 days at 28° C. Surface-disinfected seeds of different maize cultivars (Helmi, Morignon, Pelicon, Peso and Cesor) were immersed in the bacterial suspensions for 30 min. The bacterized seeds were deposited onto soft water-agar plates (0.8%, w/v agar) and plates were placed in the dark at room temperature (24±2° C.). After 96 hrs the percentage of germinated seeds was scored. Surface-sterilized seeds, but not bacterized (treated in tryptic soy broth), served as the germination control.

Inoculation of maize seeds with endophytic bacteria increased the germination rate of all cultivars by 20-40% compared to the un-inoculated control. Maximum increase was observed by inoculation with strain FD17 (40%) in maize cv. Morignon followed by strains FF34, FA13, FB12 and FC42 (data not shown).

In other experiments, seeds of different cultivars of Maize (Palazzo & die Samba), and Tomato (Red Pear and Gartenfreund) were used to test for promotion of germination. The results, provided below in Table 7, show that virtually all strains show a marked increase in germination rates. For maize, Palazzo seeds inoculated with the strains FA13, FF34, S2, S6, S9 and S10 show greater than 90% germination after four days, as did die Samba seeds inoculated with FF34 and S9 seeds. For tomato, Red Pear seeds inoculated with the strains FB12, FF34, S6 and S10 showed 90% or greater germination rate after 12 days.

TABLE 7

Germination rate of maize and tomato seeds inoculated with endophytes

| | Maize Germination Rate (4 Days) | | Tomato Germination Rate (12 days) | |
|---|---|---|---|---|
| Strain | Maize "Palazzo" | Maize "die Samba" | Tomato "Red Pear" | Tomato "Gartenfreund" |
| Neg. control | 73.3% | 73.3% | 33.3% | 50.0% |
| FA13 | 100.0% | 86.7% | 83.3% | 60.0% |
| FB12 | 83.3% | 76.7% | 96.7% | 53.3% |
| FC42 | 86.7% | 86.7% | 76.7% | 80.0% |
| FD17 | 76.7% | 66.7% | 43.3% | 46.7% |
| FF34 | 93.3% | 93.3% | 96.7% | 50.0% |
| S2 | 93.3% | 70.0% | 70.0% | 60.0% |
| S4 | 70.0% | 86.7% | 76.7% | 66.7% |
| S6 | 90.0% | 80.0% | 100.0% | 70.0% |
| S9 | 96.7% | 96.7% | 60.0% | 53.3% |
| S10 | 93.3% | 80.0% | 90.0% | 76.7% |

In Vitro Screening of Efficient Strains Under Axenic Conditions

A growth chamber experiment was conducted on maize to screen the selected strains for their growth promoting activity under gnotobiotic conditions. We used specially designed glass tubes with beaded rim (Duran group, DURAN GmbH, Mainz, Germany) for the experiment. The glass tubes were covered with lid to generate fully axenic conditions (no exposure to any environmental factors). Bacterial inoculant production and seed treatment were done as described above. As control, seeds were treated with sterilized tryptic soy broth. Treated seeds were placed onto water-agar plates for germination. After 5 days, germinated seedlings (3-5 cm long) were transferred in the sterilized glass tubes containing sterilized 20 ml MS (Murashige and Skoog) medium (Duchefa Biochemie, The Netherlands) (4.8 g L$^{-1}$) and placed at 25±2° C. set at a 16 h light and 8 h dark period, with a light intensity of 350 μmol m$^{-2}$ s$^{-1}$. Data regarding shoot/root length and biomass were recorded after 24 days. Colonization of inoculant strains was scored by re-isolation of endophytes. One g of plant shoot was homogenized with a pestle and mortar in 4 ml of 0.9% (w/v) NaCl solution. The number of cultivable endophytes in maize shoot, expressed in CFU per gram (fresh weight), was determined by spreading serial dilution up to $10^{-4}$ (0.1 mL) of homogenized surface-sterilized plant material onto TSA (DIFCO Laboratories, Detroit, Mich.) agar medium. Four replicates for each treatment were spread on the agar plates and incubated for 5 days at 28° C. Twenty colonies per treatment were randomly selected and their identity with the inoculant strain was confirmed by restriction fragment length polymorphism (RFLP) analysis of the 16S-23S rRNA intergenic spacer (IGS) region (Reiter et al. 2001, Appl Environ Microbiol 68:2261-2268, incorporated herein by reference).

All strains significantly increased the seedling growth compared to the control. As shown in FIGS. 1A-1C, all strains significantly promoted biomass production, with increases in both root, shoot or overall biomass. Though responses were variable, the strains generally increased root and shoot length in all three cultivars of maize tested.

Next, colonization of plants was tested for all bacterial strains. As shown in Table 8, strains FA13, FF34, FC42, FB12 and FD17 successfully colonized corn plants, showing successful colonization of the various strains, as detected in the shoot tissue of various cultivars of maize. The amount of detectable bacteria in the shoot tissue varied, ranging from $1.58 \times 10^4$ in FB12-inoculated Helmi cultivar, to $1.83 \times 10^7$ CFU found in Peso cultivars inoculated with FF34. Therefore, the microbes described herein, when contacted with seeds of plants, are capable of colonizing the plant as detectable, in this case, in the shoot tissue. Furthermore, colonization of Kolea, Mazurka and DaSilvie cultivars of maize by strains S2, S4, S6, S9 and S10 was confirmed by isolating bacterial cells from homogenates of surface sterilized shoot tissue of plants grown from inoculated seeds on tryptic soy agar plates for two days on 28° C. and testing the identity of colonies with IGS region sequencing to confirm the presence of the microbe. S2, S4, S6, S9 and S10 strains were successfully recovered from the tissues of these cultivars (data not shown).

TABLE 8

Colonization of Maize Plants by Endophytic Bacteria

| Strains | Helmi | Peso | Pelicon | Morignon | Cesor |
|---|---|---|---|---|---|
| FA13 | $1.95 \times 10^5$ | $1.16 \times 10^7$ | $1.2 \times 10^4$ | $1.21 \times 10^6$ | $3.31 \times 10^6$ |
| FF34 | $2.66 \times 10^6$ | $1.83 \times 10^7$ | $1.21 \times 10^5$ | $4.13 \times 10^6$ | $9.1 \times 10^6$ |
| FC42 | $4.63 \times 10^5$ | $1.37 \times 10^6$ | $2.00 \times 10^4$ | $8.24 \times 10^6$ | $1.07 \times 10^5$ |
| FB12 | $1.58 \times 10^4$ | $1.94 \times 10^7$ | $1.12 \times 10^5$ | $1.46 \times 10^6$ | $9.38 \times 10^5$ |
| FD17 | $1.92 \times 10^6$ | $2.60 \times 10^7$ | $1.44 \times 10^7$ | $2.93 \times 10^7$ | $1.73 \times 10^6$ |

Stomatal Conductance and Photosynthesis Rates

Maize plants inoculated with the strains described herein were tested for photosynthesis and stomatal conductance. As shown in FIG. 2, maize plants inoculated with the strains display an increase in stomatal conductance when compared with uninoculated controls (ranging from a 36% to 49% increase), with S2, S6, S9 strains displaying the highest level of conductance. Therefore, there is an appreciable increase in stomatal conductance conferred by the bacterial of the present invention.

Figure 3:
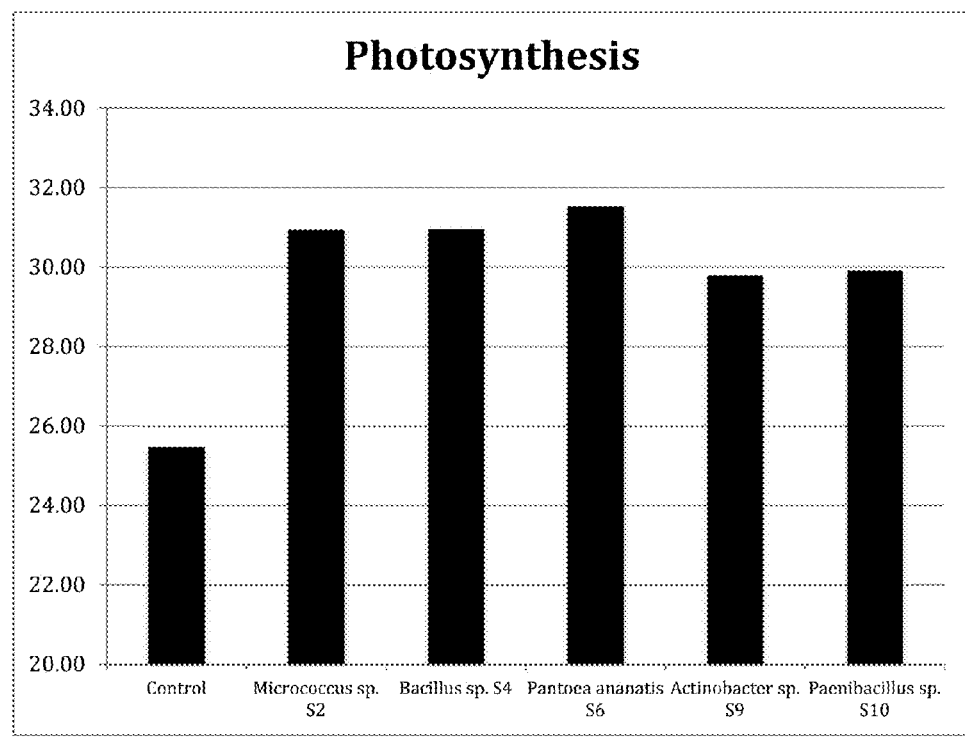
FIG. 3 shows the increase in photosynthetic rates in maize plants inoculated with the bacterial endophyte populations when compared with uninoculated control plants.

Strain-inoculated maize plants were also tested for photosynthetic rates. As shown in FIG. 3, all strains conferred increased photosynthesis rates when compared with control plants in all three maize cultivars tested (DaSilvie, Mazurka, and Kolea cultivars; average of three cultivars shown), with an increase ranging from 17% over controls (for S9 and S10 strains) to over 23% over controls (S6 strain). Therefore, the endophytic bacterial strains described above confer increased photosynthesis rates on the host plants.

Net-House Experiment

On the basis of the results from tests performed under axenic conditions, strain FD17 was selected for further evaluation in a pot trial, in which plants were grown in large containers exposed to natural environmental conditions. Maize plants were grown in soil collected from agricultural (maize) fields in Fischamend, Lower Austria, Austria. The soil was silty clay loam and had the following characteristics: 12% sand, 61% silt, 27% clay, pH 6.5, 3.3% total carbon, 0.18% total nitrogen, 0.13 mg g$^{-1}$ available phosphorus, 0.066 mg g$^{-1}$ extractable potassium.

Surface-disinfected seeds of two maize cultivars (Morignon and Peso) were immersed in bacterial suspension (prepared as described above) for 1 h. For the un-inoculated control, seeds were treated with sterilized tryptic soy broth. Seeds were sown in a plastic tray (wiped with ethanol) and 12 days old seedlings were transferred into containers filled with 45 kg soil (2 plants in each container) and placed in a net-house and exposed to natural environmental conditions.

Figure 4:
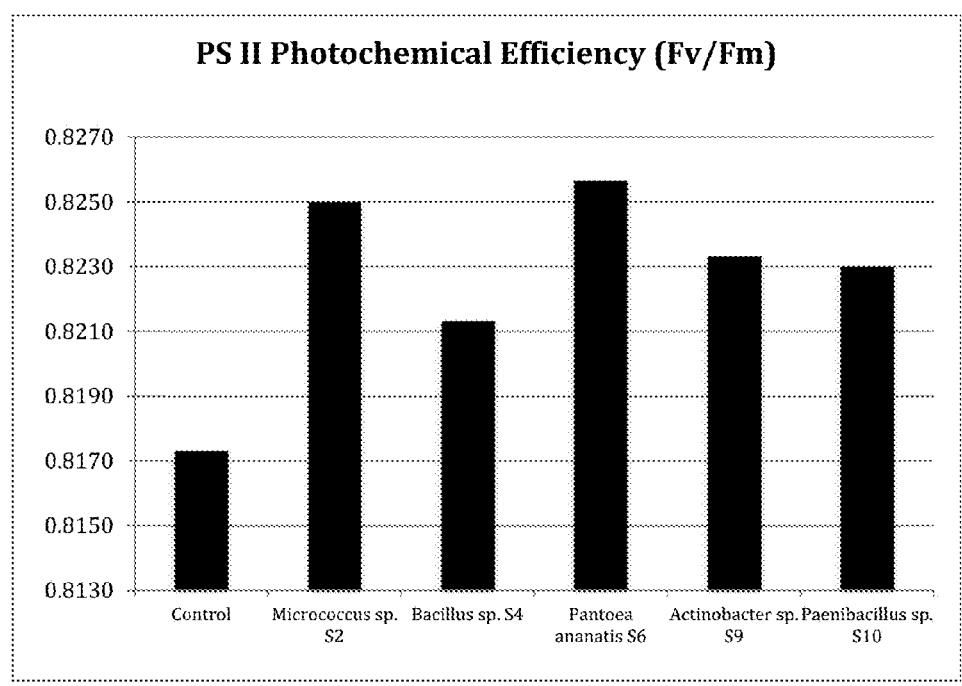
FIG. 4 shows the increases in PS II photochemical efficiency (Fv/Fm) in maize plants inoculated with the bacterial endophyte populations, when compared with uninoculated control plants.

Weather conditions i.e. precipitation, temperature and relative humidity were recorded by 'Zentralanstalt für Meteorologie and Geodynamik' (ZAMG) during the crop growth period and described in FIGS. 1A-1C. There were three replicates and the pots were arranged in a completely randomized design. Recommended dose of NPK fertilizers (160-100-60 kg ha$^{-1}$) were applied in each container and tap water was applied to the container for irrigation whenever needed. Data of photochemical efficiency of PSII was recorded at flowering stage using handy PEA (Hansatech Instruments Ltd. England) in the mid of July where day time temperature varied from 30-35° C. The PSII efficiency in terms of $F_v/F_m$ was calculated from the data. Growth and yield contributing parameters were recorded at maturity. The plants were harvested 140 days after planting. FIG. 4 shows the PS II efficiency of maize plants inoculated with the bacterial endophyte populations described herein.

Figure 5:
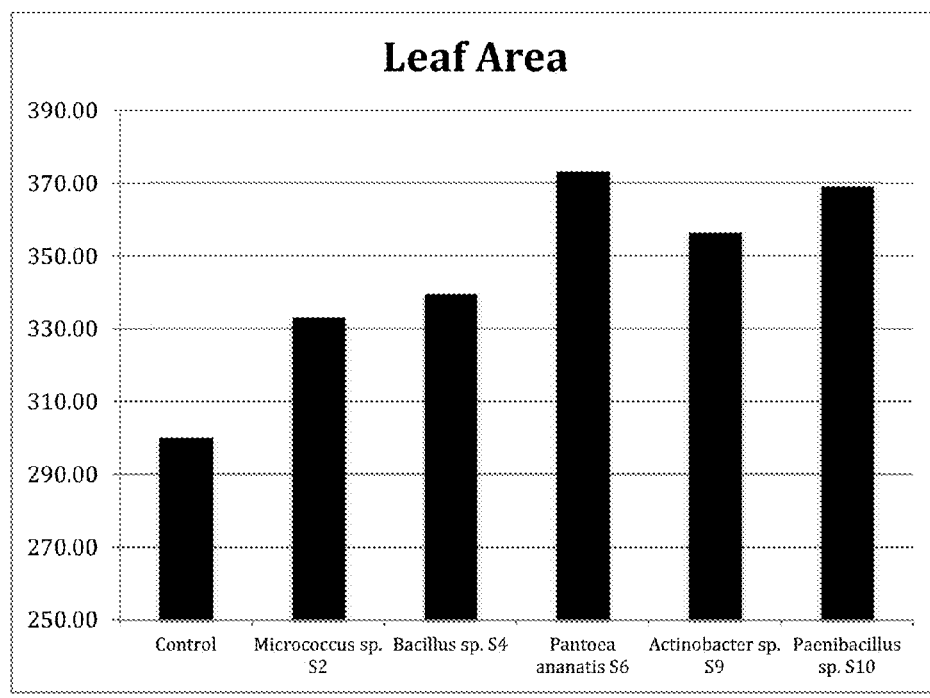
FIG. 5 shows the increases in leaf area in maize plants inoculated with the bacterial endophyte populations, when compared with uninoculated control plants.

Maize plants inoculated with the bacterial endophytes S2, S4, S6, S9, S10 and FD17 were tested for increased leaf area. As shown in FIG. 5, and in Table 9, all the tested strains increased the leaf area significantly over the controls.

Figure 6:
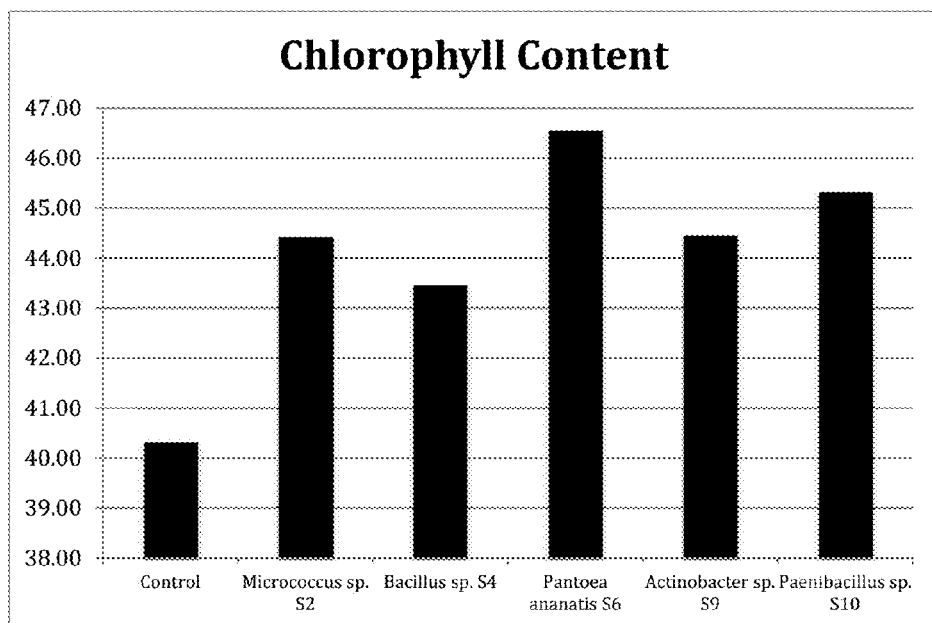
FIG. 6 shows the increases in chlorophyll content in maize plants inoculated with the bacterial endophyte populations, when compared with uninoculated control plants.

Similarly, maize plants inoculated with the strains showed a dramatic increase in chlorophyll content (FIG. 6) over control plants, with the highest levels found in S6 inoculated plants.

Table 9 below shows the effect of FD17 inoculation on the physiology, growth parameters and yield of two maize cultivars grown in field soil and exposed to natural climatic conditions. Inoculation with strain FD17 led to a significant increase in leaf area of both cultivars (20% and 13%, respectively). Similarly, biomass (leaf dry weight) was increased by 27% and 23% in the cultivars Peso and Morignon, respectively, as compared to the control. In addition, root and plant dry biomass and plant height were significantly enhanced, as was the average cob weight (35% and 42% increase in Peso and Morignon, respectively, as compared to control). The FD17 strain also significantly affected other plant physiological characteristics: for example, there was a significant increase in chlorophyll fluorescence (up to a 9% in the Peso cultivar) and a shortened time before onset of flowering (up to 10 days in cultivar Peso).

TABLE 9

Effect of inoculation with endophytic strain FD17 on physiology, growth parameters and yield of two maize cultivars grown in pots in field soil and exposed to natural climatic conditions (net house experiment)

| | Treatment | | | |
|---|---|---|---|---|
| | Peso | | Morignon | |
| Parameters | Un-inoculated | Inoculated with FD17 | Un-inoculated | Inoculated with FD17 |
| Fv/Fm | 0.69 | 0.75 | 0.73 | 0.79 |
| Time to onset of flowering (days) | 65.33 | 55 | 70.67 | 66.33 |

TABLE 9-continued

Effect of inoculation with endophytic strain FD17 on physiology, growth parameters and yield of two maize cultivars grown in pots in field soil and exposed to natural climatic conditions (net house experiment)

| Parameters | Treatment | | | |
|---|---|---|---|---|
| | Peso | | Morignon | |
| | Un-inoculated | Inoculated with FD17 | Un-inoculated | Inoculated with FD17 |
| Plant height (cm) | 192.33 | 208 | 196.69 | 213.68 |
| No. of leaves plant | 12.33 | 14 | 13.17 | 14.67 |
| Leaf area (cm$^2$) | 494.26 | 556.27 | 512.39 | 617.11 |
| Leaf dry weight (g) | 22.21 | 28.16 | 28.09 | 34.56 |
| Plant dry biomass (g) | 114.18 | 153.77 | 160.46 | 223.14 |
| Root dry biomass (g) | 17.26 | 24.34 | 19.73 | 28.28 |
| Cob weight (g) | 115.28 | 155.83 | 123.71 | 176.23 |

Rhizosphere and endophytic colonization of roots, stems and leaves by the inoculant strain were determined by plate counting using TSA plates. Root, stem and leave samples were washed, surface sterilized (as described above) and used for inoculant strain recovery (colonization). For this, samples were crushed in 0.9% (w/v) NaCl solution, shaken with a pulsifier (Microgen Bioproducts Ltd., UK) for 30 sec and different dilutions were spread on TSA plates. Bacterial colonies were counted after 4 days of incubation at 28±2° C. The selected colonies were identified and confirmed by IGS region-based RFLP analysis.

The ability of strain FD17 to colonize various tissues of the host plant, as well as the rhizosphere surrounding the plant, was examined. As shown in Table 10 below, seeds of two different maize cultivars inoculated with the FD17 strain resulted in effective, detectable colonization in the root, shoot and leaf interior. Therefore, the seeds were treated with an amount of the endophytic bacterium that is sufficient to colonize the leaf, root, and shoot tissues. Surprisingly, the rhizosphere also had significant levels of detectable FD17. This suggests that the beneficial effects of endophytic bacterial strains such as FD17 could be exerting effects externally to the plant. As described elsewhere, the bacteria described herein are capable of producing compounds which allow increased availability of limiting nutrients such as phosphate and iron. The strains could be present on the surface of the seeds in an amount sufficient to efficiently colonize the plant, but also the surrounding rhizosphere. The presence of significant amounts of detectable bacteria in the rhizosphere raises the interesting possibility that the seeds can be treated with the microbes either on its surface or inside the seed in an amount sufficient to alter the rhizosphere of the plant, thereby altering the soil around the plant, and rendering it more hospitable for the plant.

TABLE 10

Colonization of strain FD17 in rhizosphere, root, stem and leaves of two maize cultivars (wire-house experiment)

| | Plant compartment | | | |
|---|---|---|---|---|
| Maize cv. | Rhizosphere (cfu g$^{-1}$ dry wt) | Root interior (cfu g$^{-1}$ dry wt) | Shoot interior (cfu g$^{-1}$ dry wt) | Leaf interior (cfu g$^{-1}$ dry wt) |
| Peso | $4.07 \times 10^4$ | $3.39 \times 10^4$ | $1.63 \times 10^3$ | $1.16 \times 10^2$ |
| Morignon | $9.85 \times 10^4$ | $8.59 \times 10^4$ | $3.72 \times 10^3$ | $6.23 \times 10^2$ |

Statistical Analyses

The data of plant growth parameters and colonization were subjected to analyses of variance. The means were compared by Least Significant Difference (LSD) test (p<0.05) to detect statistical significance among treatment (Steel et al. 1997, Principles and procedures of statistics: A biometrical approach. 3rd ed. McGraw-Hill Book Int. Co., Singapore, incorporated herein by reference). All of the statistical analyses were conducted using SPSS software version 19 (IBM SPSS Statistics 19, USA).

The invention claimed is:

1. A method for preparing a corn seed comprising an endophytic bacterial population, said method comprising applying to an exterior surface of the corn seed a formulation comprising an endophytic bacterial population consisting essentially of an endophytic bacterium comprising a 16S rRNA nucleic acid sequence comprising a nucleic acid sequence consisting of SEQ ID NO:9.

2. The method of claim 1, the formulation comprising $10^8$-$10^9$ colony-forming units (CFU) $mL^{-1}$ of the endophytic bacterial population.

3. The method of claim 1, wherein the endophytic bacterial population is applied in an amount effective to be colonize shoot tissue of a plant grown from the seed when compared with a reference agricultural plant grown under the same conditions.

4. The method of claim 1, wherein the endophytic bacterial population is applied in an amount effective to increase photosynthetic rates of a plant grown from the seed by at least 17% when compared with a reference agricultural plant grown under the same conditions.

5. The method of claim 1, wherein the endophytic bacterial population is applied in an amount effective to increase the rate of seed germination of a plant grown from the seed by at least 20% when compared with a reference agricultural plant grown under the same conditions.

6. The method of claim 1, wherein the endophytic bacterial population is applied in an amount effective to increase the rate of seed germination of Helmi, Morignon, Pelicon, Peso and Cesor maize cultivars grown from the seed by at least 20% when compared with a reference agricultural plant grown under the same conditions.

7. The method of claim 1, wherein the endophytic bacterial population is applied in an amount effective to increase the rate of seed germination of Palazzo and die Samba maize cultivars grown from the seed by at least 32% when compared with a reference agricultural plant grown under the same conditions.

8. The method of claim 1, wherein the endophytic bacterial population is applied in an amount effective to increase root biomass of a plant grown from the seed under gnotobiotic conditions when compared with a reference agricultural plant grown under the same conditions.

9. The method of claim 1, wherein the endophytic bacterial population is applied in an amount effective to increase total biomass of a plant grown from the seed under gnotobiotic conditions when compared with a reference agricultural plant grown under the same conditions.

10. The method of claim 1, wherein the endophytic bacterial population is applied in an amount effective to colonize shoot tissue of Kolea, Mazurka and DaSilvie cultivars of maize grown from the seed when compared with a reference agricultural plant grown under the same conditions.

11. The method of claim 1, wherein the endophytic bacterial population is applied in an amount effective to increase stomatal conductance of a plant grown from the seed by 43% when compared with a reference agricultural plant grown under the same conditions.

12. The method of claim 1, wherein the endophytic bacterial population is applied in an amount effective to increase photosynthesis rates by 17% in DaSilvie, Mazurka, and Kolea cultivars grown from the seed when compared with a reference agricultural plant grown under the same conditions.

13. The method of claim 1, wherein the endophytic bacterial population is applied in an amount effective to increase photochemical efficiency of a plant grown from the seed by 7% when compared with a reference agricultural plant grown under the same conditions.

14. The method of claim 1, wherein the endophytic bacterial population is applied in an amount effective to increase leaf area of a plant grown from the seed by 18% when compared with a reference agricultural plant grown under the same conditions.

15. The method of claim 1, wherein the endophytic bacterial population is applied in an amount effective to increase chlorophyll content of a plant grown from the seed by 10% when compared with a reference agricultural plant grown under the same conditions.

16. The method of claim 1, wherein
the formulation comprises $10^8$-$10^9$ colony-forming units (CFU) $mL^{-1}$ of the endophytic bacterial population; and
the endophytic bacterial population is applied in an amount effective to increase the rate of seed germination of a plant grown from the seed when compared with a reference agricultural plant grown under the same conditions; and the endophytic bacterial population is applied in an amount effective to increase root biomass of a plant grown from the seed under gnotobiotic conditions when compared with a reference agricultural plant grown under the same conditions; and the endophytic bacterial population is applied in an amount effective to increase total biomass of a plant grown from the seed under gnotobiotic conditions when compared with a reference agricultural plant grown under the same conditions; and the endophytic bacterial population is applied in an amount effective to colonize shoot tissue of a plant grown from the seed when compared with a reference agricultural plant grown under the same conditions; and the endophytic bacterial population is applied in an amount effective to increase stomatal conductance of a plant grown from the seed when compared with a reference agricultural plant grown under the same conditions; and the endophytic bacterial population is applied in an amount effective to increase photosynthesis rates in a plant grown from the seed when compared with a reference agricultural plant grown under the same conditions; and the endophytic bacterial population is applied in an amount effective to increase photochemical efficiency of a plant grown from the seed when compared with a reference agricultural plant grown under the same conditions; and the endophytic bacterial population is applied in an amount effective to increase leaf area of a plant grown from the seed when compared with a reference agricultural plant grown under the same conditions; and the endophytic bacterial population is applied in an amount effective to increase chlorophyll content of a plant grown from the seed when compared with a reference agricultural plant grown under the same conditions.

* * * * *